United States Patent
Nakagami et al.

(10) Patent No.: US 10,543,261 B2
(45) Date of Patent: Jan. 28, 2020

(54) DNA VACCINE CONTAINING VEGF-SPECIFIC EPITOPE AND/OR ANGIOPOIETIN-2-SPECIFIC EPITOPE

(71) Applicants: OSAKA UNIVERSITY, Suita-shi, Osaka (JP); ANGES, INC., Ibaraki-shi, Osaka (JP)

(72) Inventors: Hironori Nakagami, Suita (JP); Mariko Kyutoku, Suita (JP); Ryuichi Morishita, Suita (JP); Hideki Tomioka, Ibaraki (JP)

(73) Assignees: Osaka University, Suita (JP); AnGes, Inc., Ibaraki (JP)

( * ) Notice: Subject to any disclaimer, the term of this patent is extended or adjusted under 35 U.S.C. 154(b) by 0 days.

(21) Appl. No.: 14/424,937

(22) PCT Filed: Aug. 28, 2013

(86) PCT No.: PCT/JP2013/073045
§ 371 (c)(1),
(2) Date: Feb. 27, 2015

(87) PCT Pub. No.: WO2014/034735
PCT Pub. Date: Mar. 6, 2014

(65) Prior Publication Data
US 2015/0202271 A1    Jul. 23, 2015

(30) Foreign Application Priority Data
Aug. 31, 2012   (JP) ................... 2012-191717

(51) Int. Cl.
| C12N 7/00 | (2006.01) |
| C12N 15/86 | (2006.01) |
| A61K 39/00 | (2006.01) |

(52) U.S. Cl.
CPC ............ *A61K 39/0011* (2013.01); *C12N 7/00* (2013.01); *A61K 2039/5256* (2013.01); *A61K 2039/53* (2013.01); *A61K 2039/545* (2013.01); *C12N 2730/10134* (2013.01); *C12N 2730/10143* (2013.01)

(58) Field of Classification Search
CPC .. C12N 7/00; C12N 15/1131; C12N 15/1135; C12N 2320/30; C12N 2710/00034; C12N 2710/16634; C12N 2720/12034; C12N 2730/10134; C12N 2740/16034; C12N 2740/16134; C12N 2740/16234; C12N 2760/14134; C12N 2760/18034
See application file for complete search history.

(56) References Cited

U.S. PATENT DOCUMENTS

| 2004/0054139 | A1 | 3/2004 | Page et al. |
| 2004/0223965 | A1 | 11/2004 | Gehin et al. |
| 2005/0175624 | A1 | 8/2005 | Romero et al. |
| 2006/0110400 | A1 | 5/2006 | Glover et al. |
| 2008/0267971 | A1 | 10/2008 | Green et al. |
| 2010/0111967 | A1 | 5/2010 | Baehner et al. |
| 2011/0177074 | A1* | 7/2011 | Sivakumar ............ C07K 16/22 424/136.1 |
| 2011/0236388 | A1 | 9/2011 | Baehner et al. |

FOREIGN PATENT DOCUMENTS

| CN | 1441807 A | 9/2003 |
| CN | 1646153 A | 7/2005 |
| CN | 1675241 A | 9/2005 |
| JP | 2003-530123 A | 10/2003 |
| JP | 2004-500868 A | 1/2004 |
| JP | 2006-501145 A | 1/2006 |
| JP | 2006-512049 A | 4/2006 |
| JP | 2008-523841 A | 7/2008 |
| JP | 2012-504943 A | 3/2012 |
| WO | WO 2003/086450 A1 | 10/2003 |
| WO | WO 2009/120922 A2 | 10/2009 |
| WO | WO 2011/014469 A1 | 2/2011 |
| WO | WO 2011/117329 A | 9/2011 |

OTHER PUBLICATIONS

Sequence Alignment of SEQ ID No. 2 with SEQ ID No. 559 of USPGPUB 20110177074, Search conducted on Mar. 9, 2016, 1 page.*
Kudoku et al., "Shin Kekkan Event Kiken Inshi de Aru Lipoprotein (a) [Lp(a)] ni Taisuru Shinki Chiryo Senryaku—DNA Vaccine no Kokoromi" ["Novel Therapeutic Strategy for Cardiovascular Event Risk Factor, Lipoprotein(a) [Lp(a)]—Trying DNA Vaccine"], Nippon Shinmyakukan Sado Busshitsu Gakkaishi, Kekkan, 36(1): 40, abstract Y-2 (Jan. 31, 2013).
Japanese Patent Office, International Search Report in International Patent Application No. PCT/JP2013/073045 (dated Oct. 1, 2013).
Chinese Patent Office, Office Action in Chinese Patent Application No. 201380045197.4 (dated Feb. 1, 2016).
Klamp et al., *Cancer Research*, 71(2): 516-527 (2011).
Mao et al., "Intramuscular immunization with a DNA vaccine encoding a 26-amino acid CETP epitope displayed by HBc protein and containing CpG DNA inhibits atherosclerosis in a rabbit model of atherosclerosis," *Vaccine*, 24(23): 4942-4950 (2006).

* cited by examiner

*Primary Examiner* — Channing S Mahatan

(74) *Attorney, Agent, or Firm* — Leydig, Voit & Mayer, Ltd.

(57) ABSTRACT

The present invention provides a therapeutic or prophylactic agent for cancer, containing an expression vector encoding a chimeric Hepatitis B virus core antigen polypeptide inserted with an amino acid sequence containing a specific epitope of VEGF and/or a specific epitope of angiopoietin-2, wherein the amino acid sequence containing the specific epitope is inserted between the amino acid residues 80 and 81 of the hepatitis B virus core antigen polypeptide.

18 Claims, 5 Drawing Sheets

Figure 1:
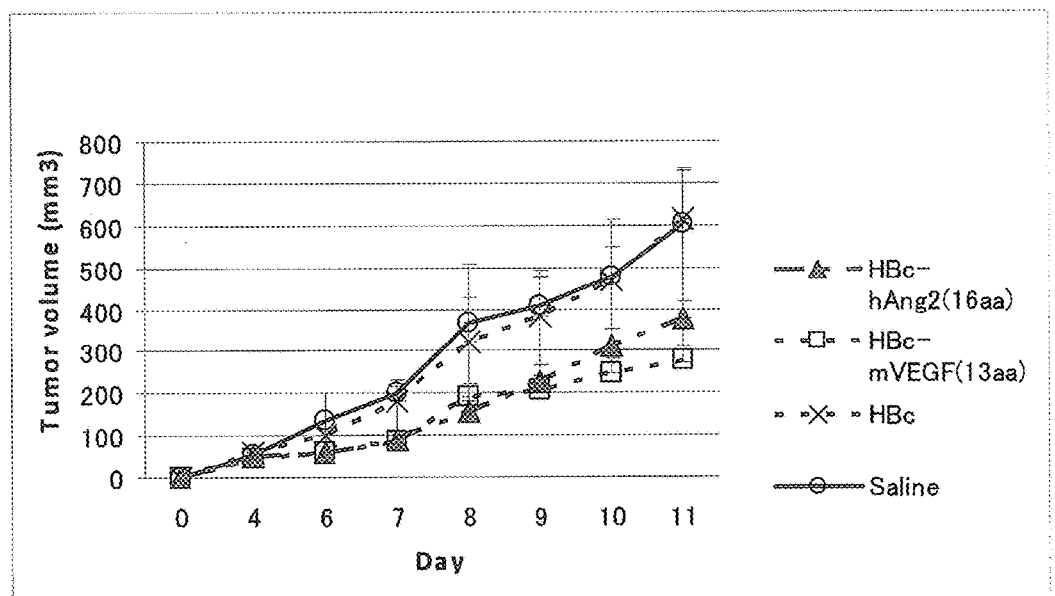

Specification includes a Sequence Listing.

SEQUENCE LISTING

```
<160> NUMBER OF SEQ ID NOS: 33

<210> SEQ ID NO 1
<211> LENGTH: 13
<212> TYPE: PRT
<213> ORGANISM: Mus musculus

<400> SEQUENCE: 1

Ile Met Arg Ile Lys Pro His Gln Ser Gln His Ile Gly
```

<210> SEQ ID NO 2
<211> LENGTH: 13
<212> TYPE: PRT
<213> ORGANISM: Homo sapiens

<400> SEQUENCE: 2

Ile Met Arg Ile Lys Pro His Gln Gly Gln His Ile Gly
1               5                   10

<210> SEQ ID NO 3
<211> LENGTH: 16
<212> TYPE: PRT
<213> ORGANISM: Homo sapiens

<400> SEQUENCE: 3

Pro Gln Arg Gln Asn Thr Asn Lys Phe Asn Gly Ile Lys Trp Tyr Tyr
1               5                   10                  15

<210> SEQ ID NO 4
<211> LENGTH: 11
<212> TYPE: PRT
<213> ORGANISM: Homo sapiens

<400> SEQUENCE: 4

Tyr Tyr Pro Gln Arg Gln Asn Thr Asn Lys Glu
1               5                   10

<210> SEQ ID NO 5
<211> LENGTH: 556
<212> TYPE: DNA
<213> ORGANISM: Hepatitis B virus
<220> FEATURE:
<221> NAME/KEY: CDS
<222> LOCATION: (2)..(553)

<400> SEQUENCE: 5

| | | |
|---|---|---|
| c atg gat atc gat cct tat aaa gaa ttc gga gct act gtg gag tta ctc<br>  Met Asp Ile Asp Pro Tyr Lys Glu Phe Gly Ala Thr Val Glu Leu Leu<br>   1               5                 10               15 | | 49 |
| tcg ttt ctc ccg agt gac ttc ttt cct tca gta cga gat ctt ctg gat<br>Ser Phe Leu Pro Ser Asp Phe Phe Pro Ser Val Arg Asp Leu Leu Asp<br>           20                25              30 | | 97 |
| acc gcc agc gcg ctg tat cgg gaa gcc ttg gag tct cct gag cac tgc<br>Thr Ala Ser Ala Leu Tyr Arg Glu Ala Leu Glu Ser Pro Glu His Cys<br>           35                40              45 | | 145 |
| agc cct cac cat act gcc ctc agg caa gca att ctt tgc tgg ggg gag<br>Ser Pro His His Thr Ala Leu Arg Gln Ala Ile Leu Cys Trp Gly Glu<br>     50                55              60 | | 193 |
| ctc atg act ctg gcc acg tgg gtg ggt gtt aac ttg gaa gat cca gct<br>Leu Met Thr Leu Ala Thr Trp Val Gly Val Asn Leu Glu Asp Pro Ala<br>65               70                75              80 | | 241 |
| agc agg gac ctg gta gtc agt tat gtc aac act aat atg ggt tta aag<br>Ser Arg Asp Leu Val Val Ser Tyr Val Asn Thr Asn Met Gly Leu Lys<br>           85                90              95 | | 289 |
| ttc agg caa ctc ttg tgg ttt cac att agc tgc ctc act ttc ggc cga<br>Phe Arg Gln Leu Leu Trp Phe His Ile Ser Cys Leu Thr Phe Gly Arg<br>          100              105            110 | | 337 |
| gaa aca gtt cta gaa tat ttg gtg tct ttc gga gtg tgg atc cgc act<br>Glu Thr Val Leu Glu Tyr Leu Val Ser Phe Gly Val Trp Ile Arg Thr<br>          115              120            125 | | 385 |
| cct cca gct tat agg cct ccg aat gcc cct atc ctg tcg aca ctc ccg | | 433 |

```
Pro Pro Ala Tyr Arg Pro Pro Asn Ala Pro Ile Leu Ser Thr Leu Pro
        130                 135                 140 gag act act gtt gtt aga cgt cga ggc agg tca cct aga aga aga act    481
Glu Thr Thr Val Val Arg Arg Arg Gly Arg Ser Pro Arg Arg Arg Thr
145                 150                 155                 160 cct tcg cct cgc agg cga agg tct caa tcg ccg cgg cgc aga tct        529
Pro Ser Pro Arg Arg Arg Arg Ser Gln Ser Pro Arg Arg Arg Ser
                165                 170                 175 caa tct cgg gaa tct caa tgt tag tga                                556
Gln Ser Arg Glu Ser Gln Cys
            180
```

<210> SEQ ID NO 6
<211> LENGTH: 183
<212> TYPE: PRT
<213> ORGANISM: Hepatitis B virus

<400> SEQUENCE: 6

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Ser
                165                 170                 175

Gln Ser Arg Glu Ser Gln Cys
            180
```

<210> SEQ ID NO 7
<211> LENGTH: 185
<212> TYPE: PRT
<213> ORGANISM: Hepatitis B virus

<400> SEQUENCE: 7

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60
```

```
Leu Met Thr Leu Ala Thr Trp Val Gly Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185
```

```
<210> SEQ ID NO 8
<211> LENGTH: 22
<212> TYPE: DNA
<213> ORGANISM: Artificial Sequence
<220> FEATURE:
<223> OTHER INFORMATION: Synthetic CpG-B 1018

<400> SEQUENCE: 8
tgactgtgaa cgttcgagat ga                                            22

<210> SEQ ID NO 9
<211> LENGTH: 20
<212> TYPE: DNA
<213> ORGANISM: Artificial Sequence
<220> FEATURE:
<223> OTHER INFORMATION: Synthetic CpG-A  D19

<400> SEQUENCE: 9
ggtgcatcga tgcagggggg                                               20

<210> SEQ ID NO 10
<211> LENGTH: 21
<212> TYPE: DNA
<213> ORGANISM: Artificial Sequence
<220> FEATURE:
<223> OTHER INFORMATION: Synthetic CpG-C C274

<400> SEQUENCE: 10
tcgtcgaacg ttcgagatga t                                             21

<210> SEQ ID NO 11
<211> LENGTH: 25
<212> TYPE: DNA
<213> ORGANISM: Artificial Sequence
<220> FEATURE:
<223> OTHER INFORMATION: Synthetic CpG-C C695

<400> SEQUENCE: 11
tcgaacgttc gaacgttcga acgtt                                         25

<210> SEQ ID NO 12
<211> LENGTH: 88
<212> TYPE: DNA
<213> ORGANISM: Artificial Sequence
<220> FEATURE:
<223> OTHER INFORMATION: ISS
```

<400> SEQUENCE: 12

```
ggtgcatcga tgcagggggg tgactgtgaa cgttcgagat gatcgtcgaa cgttcgagat    60
gattcgaacg ttcgaacgtt cgaacgtt                                       88
```

<210> SEQ ID NO 13
<211> LENGTH: 232
<212> TYPE: PRT
<213> ORGANISM: Homo sapiens

<400> SEQUENCE: 13

```
Met Asn Phe Leu Leu Ser Trp Val His Trp Ser Leu Ala Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

<210> SEQ ID NO 14
<211> LENGTH: 207
<212> TYPE: PRT
<213> ORGANISM: Homo sapiens

<400> SEQUENCE: 14

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60
```

```
Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
            115                 120                 125

Lys Asp Ser Ala Val Lys Pro Asp Arg Ala Ala Thr Pro His His Arg
130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
            195                 200                 205

<210> SEQ ID NO 15
<211> LENGTH: 419
<212> TYPE: PRT
<213> ORGANISM: Homo sapiens

<400> SEQUENCE: 15

Met His Leu Leu Gly Phe Phe Ser Val Ala Cys Ser Leu Leu Ala Ala
 1               5                  10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
 50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                 85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
            195                 200                 205

Cys Arg Cys Met Ser Lys Leu Asp Val Tyr Arg Gln Val His Ser Ile
210                 215                 220

Ile Arg Arg Ser Leu Pro Ala Thr Leu Pro Gln Cys Gln Ala Ala Asn
```

```
            225                 230                 235                 240

Lys Thr Cys Pro Thr Asn Tyr Met Trp Asn Asn His Ile Cys Arg Cys
                    245                 250                 255

Leu Ala Gln Glu Asp Phe Met Phe Ser Ser Asp Ala Gly Asp Asp Ser
                260                 265                 270

Thr Asp Gly Phe His Asp Ile Cys Gly Pro Asn Lys Glu Leu Asp Glu
            275                 280                 285

Glu Thr Cys Gln Cys Val Cys Arg Ala Gly Leu Arg Pro Ala Ser Cys
        290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                    325                 330                 335

Asn Thr Cys Gln Cys Val Cys Lys Arg Thr Cys Pro Arg Asn Gln Pro
                340                 345                 350

Leu Asn Pro Gly Lys Cys Ala Cys Glu Cys Thr Glu Ser Pro Gln Lys
            355                 360                 365

Cys Leu Leu Lys Gly Lys Lys Phe His His Gln Thr Cys Ser Cys Tyr
        370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                    405                 410                 415

Gln Met Ser

<210> SEQ ID NO 16
<211> LENGTH: 354
<212> TYPE: PRT
<213> ORGANISM: Homo sapiens

<400> SEQUENCE: 16

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
                20                  25                  30

Ser Gln Ser Thr Leu Glu Arg Ser Glu Gln Gln Ile Arg Ala Ala Ser
            35                  40                  45

Ser Leu Glu Glu Leu Leu Arg Ile Thr His Ser Glu Asp Trp Lys Leu
        50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
                100                 105                 110

Pro Arg Glu Thr Cys Val Glu Val Ala Ser Glu Leu Gly Lys Ser Thr
            115                 120                 125

Asn Thr Phe Phe Lys Pro Pro Cys Val Asn Val Phe Arg Cys Gly Gly
        130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
```

```
                180             185             190
Pro Thr Ala Pro Arg His Pro Tyr Ser Ile Ile Arg Arg Ser Ile Gln
            195                 200                 205
Ile Pro Glu Glu Asp Arg Cys Ser His Ser Lys Lys Leu Cys Pro Ile
210                 215                 220
Asp Met Leu Trp Asp Ser Asn Lys Cys Lys Cys Val Leu Gln Glu Glu
225                 230                 235                 240
Asn Pro Leu Ala Gly Thr Glu Asp His Ser His Leu Gln Glu Pro Ala
            245                 250                 255
Leu Cys Gly Pro His Met Met Phe Asp Glu Asp Arg Cys Glu Cys Val
            260                 265                 270
Cys Lys Thr Pro Cys Pro Lys Asp Leu Ile Gln His Pro Lys Asn Cys
            275                 280                 285
Ser Cys Phe Glu Cys Lys Glu Ser Leu Glu Thr Cys Cys Gln Lys His
            290                 295                 300
Lys Leu Phe His Pro Asp Thr Cys Ser Cys Glu Asp Arg Cys Pro Phe
305                 310                 315                 320
His Thr Arg Pro Cys Ala Ser Gly Lys Thr Ala Cys Ala Lys His Cys
                325                 330                 335
Arg Phe Pro Lys Glu Lys Arg Ala Ala Gln Gly Pro His Ser Arg Lys
            340                 345                 350
Asn Pro
```

<210> SEQ ID NO 17
<211> LENGTH: 345
<212> TYPE: PRT
<213> ORGANISM: Homo sapiens

<400> SEQUENCE: 17

```
Met Ser Leu Phe Gly Leu Leu Leu Leu Thr Ser Ala Leu Ala Gly Gln
1               5                   10                  15
Arg Gln Gly Thr Gln Ala Glu Ser Asn Leu Ser Ser Lys Phe Gln Phe
            20                  25                  30
Ser Ser Asn Lys Glu Gln Asn Gly Val Gln Asp Pro Gln His Glu Arg
            35                  40                  45
Ile Ile Thr Val Ser Thr Asn Gly Ser Ile His Ser Pro Arg Phe Pro
50                  55                  60
His Thr Tyr Pro Arg Asn Thr Val Leu Val Trp Arg Leu Val Ala Val
65                  70                  75                  80
Glu Glu Asn Val Trp Ile Gln Leu Thr Phe Asp Glu Arg Phe Gly Leu
                85                  90                  95
Glu Asp Pro Glu Asp Asp Ile Cys Lys Tyr Asp Phe Val Glu Val Glu
            100                 105                 110
Glu Pro Ser Asp Gly Thr Ile Leu Gly Arg Trp Cys Gly Ser Gly Thr
            115                 120                 125
Val Pro Gly Lys Gln Ile Ser Lys Gly Asn Gln Ile Arg Ile Arg Phe
            130                 135                 140
Val Ser Asp Glu Tyr Phe Pro Ser Glu Pro Gly Phe Cys Ile His Tyr
145                 150                 155                 160
Asn Ile Val Met Pro Gln Phe Thr Glu Ala Val Ser Pro Ser Val Leu
                165                 170                 175
Pro Pro Ser Ala Leu Pro Leu Asp Leu Leu Asn Asn Ala Ile Thr Ala
            180                 185                 190
Phe Ser Thr Leu Glu Asp Leu Ile Arg Tyr Leu Glu Pro Glu Arg Trp
```

```
            195                 200                 205
Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Asn Cys Ala Cys Cys Leu
                275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
                340                 345

<210> SEQ ID NO 18
<211> LENGTH: 221
<212> TYPE: PRT
<213> ORGANISM: Homo sapiens

<400> SEQUENCE: 18

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
                20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
                100                 105                 110

Asp Arg Pro Ser Tyr Val Glu Leu Thr Phe Ser Gln His Val Arg Cys
        115                 120                 125

Glu Cys Arg His Ser Pro Gly Arg Gln Ser Pro Asp Met Pro Gly Asp
    130                 135                 140

Phe Arg Ala Asp Ala Pro Ser Phe Leu Pro Pro Arg Arg Ser Leu Pro
145                 150                 155                 160

Met Leu Phe Arg Met Glu Trp Gly Cys Ala Leu Thr Gly Ser Gln Ser
                165                 170                 175

Ala Val Trp Pro Ser Ser Pro Val Pro Glu Glu Ile Pro Arg Met His
                180                 185                 190

Pro Gly Arg Asn Gly Lys Lys Gln Gln Arg Lys Pro Leu Arg Glu Lys
            195                 200                 205

Met Lys Pro Glu Arg Cys Gly Asp Ala Val Pro Arg Arg
    210                 215                 220
```

<210> SEQ ID NO 19
<211> LENGTH: 214
<212> TYPE: PRT
<213> ORGANISM: Mus musculus

<400> SEQUENCE: 19

Met Asn Phe Leu Leu Ser Trp Val His Trp Thr Leu Ala Leu Leu Leu
1               5                   10                  15

Tyr Leu His His Ala Lys Trp Ser Gln Ala Ala Pro Thr Thr Glu Gly
                20                  25                  30

Glu Gln Lys Ser His Glu Val Ile Lys Phe Met Asp Val Tyr Gln Arg
            35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Ala Gly Cys Cys Asn Asp Glu Ala Leu Glu Cys Val Pro Thr
                85                  90                  95

Ser Glu Ser Asn Ile Thr Met Gln Ile Met Arg Ile Lys Pro His Gln
            100                 105                 110

Ser Gln His Ile Gly Glu Met Ser Phe Leu Gln His Ser Arg Cys Glu
        115                 120                 125

Cys Arg Pro Lys Lys Asp Arg Thr Lys Pro Glu Lys Lys Ser Val Arg
    130                 135                 140

Gly Lys Gly Lys Gly Gln Lys Arg Lys Arg Lys Lys Ser Arg Phe Lys
145                 150                 155                 160

Ser Trp Ser Val His Cys Glu Pro Cys Ser Glu Arg Arg Lys His Leu
                165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
        195                 200                 205

Cys Asp Lys Pro Arg Arg
    210

<210> SEQ ID NO 20
<211> LENGTH: 207
<212> TYPE: PRT
<213> ORGANISM: Mus musculus

<400> SEQUENCE: 20

Met Ser Pro Leu Leu Arg Arg Leu Leu Leu Val Ala Leu Leu Gln Leu
1               5                   10                  15

Ala Arg Thr Gln Ala Pro Val Ser Gln Phe Asp Gly Pro Ser His Gln
                20                  25                  30

Lys Lys Val Val Pro Trp Ile Asp Val Tyr Ala Arg Ala Thr Cys Gln
            35                  40                  45

Pro Arg Glu Val Val Val Pro Leu Ser Met Glu Leu Met Gly Asn Val
    50                  55                  60

Val Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Gln Tyr Pro Ser Ser Gln Leu Gly
            100                 105                 110

```
Glu Met Ser Leu Glu Glu His Ser Gln Cys Glu Cys Arg Pro Lys Lys
            115                 120                 125

Lys Glu Ser Ala Val Lys Pro Asp Arg Val Ala Ile Pro His His Arg
    130                 135                 140

Pro Gln Pro Arg Ser Val Pro Gly Trp Asp Ser Thr Pro Gly Ala Ser
145                 150                 155                 160

Ser Pro Ala Asp Ile Ile His Pro Thr Pro Ala Pro Gly Ser Ser Ala
                165                 170                 175

Arg Leu Ala Pro Ser Ala Val Asn Ala Leu Thr Pro Gly Pro Ala Ala
            180                 185                 190

Ala Ala Ala Asp Ala Ala Ala Ser Ser Ile Ala Lys Gly Gly Ala
            195                 200                 205

<210> SEQ ID NO 21
<211> LENGTH: 415
<212> TYPE: PRT
<213> ORGANISM: Mus musculus

<400> SEQUENCE: 21

Met His Leu Leu Cys Phe Leu Ser Leu Ala Cys Ser Leu Leu Ala Ala
1               5                   10                  15

Ala Leu Ile Pro Ser Pro Arg Glu Ala Pro Ala Thr Val Ala Ala Phe
            20                  25                  30

Glu Ser Gly Leu Gly Phe Ser Glu Ala Glu Pro Asp Gly Gly Glu Val
        35                  40                  45

Lys Ala Phe Glu Gly Lys Asp Leu Glu Glu Gln Leu Arg Ser Val Ser
    50                  55                  60

Ser Val Asp Glu Leu Met Ser Val Leu Tyr Pro Asp Tyr Trp Lys Met
65                  70                  75                  80

Tyr Lys Cys Gln Leu Arg Lys Gly Gly Trp Gln Gln Pro Thr Leu Asn
                85                  90                  95

Thr Arg Thr Gly Asp Ser Val Lys Phe Ala Ala Ala His Tyr Asn Thr
            100                 105                 110

Glu Ile Leu Lys Ser Ile Asp Asn Glu Trp Arg Lys Thr Gln Cys Met
        115                 120                 125

Pro Arg Glu Val Cys Ile Asp Val Gly Lys Glu Phe Gly Ala Ala Thr
    130                 135                 140

Asn Thr Phe Phe Lys Pro Pro Cys Val Ser Val Tyr Arg Cys Gly Gly
145                 150                 155                 160

Cys Cys Asn Ser Glu Gly Leu Gln Cys Met Asn Thr Ser Thr Gly Tyr
                165                 170                 175

Leu Ser Lys Thr Leu Phe Glu Ile Thr Val Pro Leu Ser Gln Gly Pro
            180                 185                 190

Lys Pro Val Thr Ile Ser Phe Ala Asn His Thr Ser Cys Arg Cys Met
        195                 200                 205

Ser Lys Leu Asp Val Tyr Arg Gln Val His Ser Ile Ile Arg Arg Ser
    210                 215                 220

Leu Pro Ala Thr Leu Pro Gln Cys Gln Ala Ala Asn Lys Thr Cys Pro
225                 230                 235                 240

Thr Asn Tyr Val Trp Asn Asn Tyr Met Cys Arg Cys Leu Ala Gln Gln
                245                 250                 255

Asp Phe Ile Phe Tyr Ser Asn Val Glu Asp Asp Ser Thr Asn Gly Phe
            260                 265                 270

His Asp Val Cys Gly Pro Asn Lys Glu Leu Asp Glu Asp Thr Cys Gln
        275                 280                 285
```

```
Cys Val Cys Lys Gly Gly Leu Arg Pro Ser Ser Cys Gly Pro His Lys
            290                 295                 300

Glu Leu Asp Arg Asp Ser Cys Gln Cys Val Cys Lys Asn Lys Leu Phe
305                 310                 315                 320

Pro Asn Ser Cys Gly Ala Asn Arg Glu Phe Asp Glu Asn Thr Cys Gln
                325                 330                 335

Cys Val Cys Lys Arg Thr Cys Pro Arg Asn Gln Pro Leu Asn Pro Gly
                340                 345                 350

Lys Cys Ala Cys Glu Cys Thr Glu Asn Thr Gln Lys Cys Phe Leu Lys
                355                 360                 365

Gly Lys Lys Phe His His Gln Thr Cys Ser Cys Tyr Arg Arg Pro Cys
            370                 375                 380

Ala Asn Arg Leu Lys His Cys Asp Pro Gly Leu Ser Phe Ser Glu Glu
385                 390                 395                 400

Val Cys Arg Cys Val Pro Ser Tyr Trp Lys Arg Pro His Leu Asn
                405                 410                 415

<210> SEQ ID NO 22
<211> LENGTH: 358
<212> TYPE: PRT
<213> ORGANISM: Mus musculus

<400> SEQUENCE: 22

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
            20                  25                  30

Ser Phe Glu Arg Ser Ser Arg Ser Met Leu Glu Arg Ser Glu Gln Gln
            35                  40                  45

Ile Arg Ala Ala Ser Ser Leu Glu Glu Leu Leu Gln Ile Ala His Ser
        50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
                100                 105                 110

Arg Thr Gln Cys Ser Pro Arg Glu Thr Cys Val Glu Val Ala Ser Glu
            115                 120                 125

Leu Gly Lys Thr Thr Asn Thr Phe Phe Lys Pro Pro Cys Val Asn Val
            130                 135                 140

Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
            195                 200                 205

Arg Arg Ser Ile Gln Thr Pro Glu Glu Asp Glu Cys Pro His Ser Lys
        210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
```

```
            245                 250                 255
Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
            275                 280                 285

His Pro Glu Asn Cys Ser Cys Phe Glu Cys Lys Glu Ser Leu Glu Ser
            290                 295                 300

Cys Cys Gln Lys His Lys Ile Phe His Pro Asp Thr Cys Ser Cys Glu
305                 310                 315                 320

Asp Arg Cys Pro Phe His Thr Arg Thr Cys Ala Ser Arg Lys Pro Ala
                    325                 330                 335

Cys Gly Lys His Trp Arg Phe Pro Lys Glu Thr Arg Ala Gln Gly Leu
                    340                 345                 350

Tyr Ser Gln Glu Asn Pro
                355

<210> SEQ ID NO 23
<211> LENGTH: 345
<212> TYPE: PRT
<213> ORGANISM: Mus musculus

<400> SEQUENCE: 23

Met Leu Leu Leu Gly Leu Leu Leu Thr Ser Ala Leu Ala Gly Gln
1               5                   10                  15

Arg Thr Gly Thr Arg Ala Glu Ser Asn Leu Ser Ser Lys Leu Gln Leu
            20                  25                  30

Ser Ser Asp Lys Glu Gln Asn Gly Val Gln Asp Pro Arg His Glu Arg
            35                  40                  45

Val Val Thr Ile Ser Gly Asn Gly Ser Ile His Ser Pro Lys Phe Pro
            50                  55                  60

His Thr Tyr Pro Arg Asn Met Val Leu Val Trp Arg Leu Val Ala Val
65                  70                  75                  80

Asp Glu Asn Val Arg Ile Gln Leu Thr Phe Asp Glu Arg Phe Gly Leu
                    85                  90                  95

Glu Asp Pro Glu Asp Asp Ile Cys Lys Tyr Asp Phe Val Glu Val Glu
            100                 105                 110

Glu Pro Ser Asp Gly Ser Val Leu Gly Arg Trp Cys Gly Ser Gly Thr
            115                 120                 125

Val Pro Gly Lys Gln Thr Ser Lys Gly Asn His Ile Arg Ile Arg Phe
            130                 135                 140

Val Ser Asp Glu Tyr Phe Pro Ser Glu Pro Gly Phe Cys Ile His Tyr
145                 150                 155                 160

Ser Ile Ile Met Pro Gln Val Thr Glu Thr Thr Ser Pro Ser Val Leu
                    165                 170                 175

Pro Pro Ser Ser Leu Ser Leu Asp Leu Leu Asn Asn Ala Val Thr Ala
            180                 185                 190

Phe Ser Thr Leu Glu Glu Leu Ile Arg Tyr Leu Glu Pro Asp Arg Trp
            195                 200                 205

Gln Val Asp Leu Asp Ser Leu Tyr Lys Pro Thr Trp Gln Leu Leu Gly
            210                 215                 220

Lys Ala Phe Leu Tyr Gly Lys Ser Lys Val Val Asn Leu Asn Leu
225                 230                 235                 240

Leu Lys Glu Glu Val Lys Leu Tyr Ser Cys Thr Pro Arg Asn Phe Ser
                    245                 250                 255
```

```
Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Arg Lys Val Thr Lys Lys
    290                 295                 300

Tyr His Glu Val Leu Gln Leu Arg Pro Lys Thr Gly Val Lys Gly Leu
305                 310                 315                 320

His Lys Ser Leu Thr Asp Val Ala Leu Glu His His Glu Glu Cys Asp
                325                 330                 335

Cys Val Cys Arg Gly Asn Ala Gly Gly
            340                 345

<210> SEQ ID NO 24
<211> LENGTH: 158
<212> TYPE: PRT
<213> ORGANISM: Mus musculus

<400> SEQUENCE: 24

Met Leu Val Met Lys Leu Phe Thr Cys Phe Leu Gln Val Leu Ala Gly
1               5                   10                  15

Leu Ala Val His Ser Gln Gly Ala Leu Ser Ala Gly Asn Asn Ser Thr
                20                  25                  30

Glu Val Glu Val Pro Phe Asn Glu Val Trp Gly Arg Ser Tyr Cys
            35                  40                  45

Arg Pro Met Glu Lys Leu Val Tyr Ile Leu Asp Glu Tyr Pro Asp Glu
        50                  55                  60

Val Ser His Ile Phe Ser Pro Ser Cys Val Leu Leu Ser Arg Cys Ser
65                  70                  75                  80

Gly Cys Cys Gly Asp Glu Gly Leu His Cys Val Pro Ile Lys Thr Ala
                85                  90                  95

Asn Ile Thr Met Gln Ile Leu Lys Ile Pro Pro Asn Arg Asp Pro His
            100                 105                 110

Phe Tyr Val Glu Met Thr Phe Ser Gln Asp Val Leu Cys Glu Cys Arg
        115                 120                 125

Pro Ile Leu Glu Thr Thr Lys Ala Glu Arg Arg Lys Thr Lys Gly Lys
    130                 135                 140

Arg Lys Arg Ser Arg Asn Ser Gln Thr Glu Glu Pro His Pro
145                 150                 155

<210> SEQ ID NO 25
<211> LENGTH: 496
<212> TYPE: PRT
<213> ORGANISM: Homo sapiens

<400> SEQUENCE: 25

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Pro Tyr Val Ser Asn Ala
        50                  55                  60

Val Gln Arg Asp Ala Pro Leu Glu Tyr Asp Asp Ser Val Gln Arg Leu
65                  70                  75                  80
```

```
Gln Val Leu Glu Asn Ile Met Glu Asn Asn Thr Gln Trp Leu Met Lys
                85                  90                  95
Leu Glu Asn Tyr Ile Gln Asp Asn Met Lys Lys Glu Met Val Glu Ile
            100                 105                 110
Gln Gln Asn Ala Val Gln Asn Gln Thr Ala Val Met Ile Glu Ile Gly
        115                 120                 125
Thr Asn Leu Leu Asn Gln Thr Ala Glu Gln Thr Arg Lys Leu Thr Asp
    130                 135                 140
Val Glu Ala Gln Val Leu Asn Gln Thr Thr Arg Leu Glu Leu Gln Leu
145                 150                 155                 160
Leu Glu His Ser Leu Ser Thr Asn Lys Leu Glu Lys Gln Ile Leu Asp
                165                 170                 175
Gln Thr Ser Glu Ile Asn Lys Leu Gln Asp Lys Asn Ser Phe Leu Glu
            180                 185                 190
Lys Lys Val Leu Ala Met Glu Asp Lys His Ile Ile Gln Leu Gln Ser
        195                 200                 205
Ile Lys Glu Glu Lys Asp Gln Leu Gln Val Leu Val Ser Lys Gln Asn
    210                 215                 220
Ser Ile Ile Glu Glu Leu Glu Lys Lys Ile Val Thr Ala Thr Val Asn
225                 230                 235                 240
Asn Ser Val Leu Gln Lys Gln His Asp Leu Met Glu Thr Val Asn
                245                 250                 255
Asn Leu Leu Thr Met Met Ser Thr Ser Asn Ser Ala Lys Asp Pro Thr
                260                 265                 270
Val Ala Lys Glu Glu Gln Ile Ser Phe Arg Asp Cys Ala Glu Val Phe
        275                 280                 285
Lys Ser Gly His Thr Thr Asn Gly Ile Tyr Thr Leu Thr Phe Pro Asn
    290                 295                 300
Ser Thr Glu Glu Ile Lys Ala Tyr Cys Asp Met Glu Ala Gly Gly Gly
305                 310                 315                 320
Gly Trp Thr Ile Ile Gln Arg Arg Glu Asp Gly Ser Val Asp Phe Gln
                325                 330                 335
Arg Thr Trp Lys Glu Tyr Lys Val Gly Phe Gly Asn Pro Ser Gly Glu
            340                 345                 350
Tyr Trp Leu Gly Asn Glu Phe Val Ser Gln Leu Thr Asn Gln Gln Arg
        355                 360                 365
Tyr Val Leu Lys Ile His Leu Lys Asp Trp Glu Gly Asn Glu Ala Tyr
    370                 375                 380
Ser Leu Tyr Glu His Phe Tyr Leu Ser Ser Glu Glu Leu Asn Tyr Arg
385                 390                 395                 400
Ile His Leu Lys Gly Leu Thr Gly Thr Ala Gly Lys Ile Ser Ser Ile
                405                 410                 415
Ser Gln Pro Gly Asn Asp Phe Ser Thr Lys Asp Gly Asp Asn Asp Lys
            420                 425                 430
Cys Ile Cys Lys Cys Ser Gln Met Leu Thr Gly Gly Trp Trp Phe Asp
        435                 440                 445
Ala Cys Gly Pro Ser Asn Leu Asn Gly Met Tyr Tyr Pro Gln Arg Gln
    450                 455                 460
Asn Thr Asn Lys Phe Asn Gly Ile Lys Trp Tyr Tyr Trp Lys Gly Ser
465                 470                 475                 480
Gly Tyr Ser Leu Lys Ala Thr Thr Met Met Ile Arg Pro Ala Asp Phe
                485                 490                 495
```

<210> SEQ ID NO 26
<211> LENGTH: 496
<212> TYPE: PRT
<213> ORGANISM: Mus musculus

<400> SEQUENCE: 26

Met Trp Gln Ile Ile Phe Leu Thr Phe Gly Trp Asp Leu Val Leu Ala
1               5                   10                  15

Ser Ala Tyr Ser Asn Phe Arg Lys Ser Val Asp Ser Thr Gly Arg Arg
            20                  25                  30

Gln Tyr Gln Val Gln Asn Gly Pro Cys Ser Tyr Thr Phe Leu Leu Pro
        35                  40                  45

Glu Thr Asp Ser Cys Arg Ser Ser Ser Pro Tyr Met Ser Asn Ala
    50                  55                  60

Val Gln Arg Asp Ala Pro Leu Asp Tyr Asp Ser Val Gln Arg Leu
65                  70                  75                  80

Gln Val Leu Glu Asn Ile Leu Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Val Val Asn Gln Thr Ala Val Met Ile Glu Ile Gly
        115                 120                 125

Thr Ser Leu Leu Asn Gln Thr Ala Ala Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Gln His Ser Ile Ser Thr Asn Lys Leu Glu Lys Gln Ile Leu Asp
                165                 170                 175

Gln Thr Ser Glu Ile Asn Lys Leu Gln Asn Lys Asn Ser Phe Leu Glu
            180                 185                 190

Gln Lys Val Leu Asp Met Glu Gly Lys His Ser Glu Gln Leu Gln Ser
        195                 200                 205

Met Lys Glu Gln Lys Asp Glu Leu Gln Val Leu Val Ser Lys Gln Ser
    210                 215                 220

Ser Val Ile Asp Glu Leu Glu Lys Lys Leu Val Thr Ala Thr Val Asn
225                 230                 235                 240

Asn Ser Leu Leu Gln Lys Gln Gln His Asp Leu Met Glu Thr Val Asn
                245                 250                 255

Ser Leu Leu Thr Met Met Ser Ser Pro Asn Ser Lys Ser Ser Val Ala
            260                 265                 270

Ile Arg Lys Glu Glu Gln Thr Thr Phe Arg Asp Cys Ala Glu Ile Phe
        275                 280                 285

Lys Ser Gly Leu Thr Thr Ser Gly Ile Tyr Thr Leu Thr Phe Pro Asn
    290                 295                 300

Ser Thr Glu Glu Ile Lys Ala Tyr Cys Asp Met Asp Val Gly Gly Gly
305                 310                 315                 320

Gly Trp Thr Val Ile Gln His Arg Glu Asp Gly Ser Val Asp Phe Gln
                325                 330                 335

Arg Thr Trp Lys Glu Tyr Lys Glu Gly Phe Gly Ser Pro Leu Gly Glu
            340                 345                 350

Tyr Trp Leu Gly Asn Glu Phe Val Ser Gln Leu Thr Gly Gln His Arg
        355                 360                 365

Tyr Val Leu Lys Ile Gln Leu Lys Asp Trp Glu Gly Asn Glu Ala His
    370                 375                 380

-continued

```
Ser Leu Tyr Asp His Phe Tyr Leu Ala Gly Glu Glu Ser Asn Tyr Arg
385                 390                 395                 400

Ile His Leu Thr Gly Leu Thr Gly Thr Ala Gly Lys Ile Ser Ser Ile
            405                 410                 415

Ser Gln Pro Gly Ser Asp Phe Ser Thr Lys Asp Ser Asp Asn Asp Lys
        420                 425                 430

Cys Ile Cys Lys Cys Ser Gln Met Leu Ser Gly Gly Trp Trp Phe Asp
            435                 440                 445

Ala Cys Gly Pro Ser Asn Leu Asn Gly Gln Tyr Tyr Pro Gln Lys Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 27
<211> LENGTH: 618
<212> TYPE: DNA
<213> ORGANISM: Artificial Sequence
<220> FEATURE:
<223> OTHER INFORMATION: Synthetic HBc-mVEGF chimera antig

```
Arg Arg Thr Pro Ser Pro Arg Arg Arg Ser Gln Ser Pro Arg Arg
                180                 185                 190 cga aga tct caa tct cgg gaa tct caa tgt tag tgagaggcc          618
Arg Arg Ser Gln Ser Arg Glu Ser Gln Cys
        195                 200

<210> SEQ ID NO 28
<211> LENGTH: 201
<212> TYPE: PRT
<213> ORGANISM: Artificial Sequence
<220> FEATURE:
<223> OTHER INFORMATION: Synthetic Construct

<400> SEQUENCE: 28

Met Asp Ile Asp Pro Tyr Lys Glu Phe Gly Ala Thr Val Glu Leu
1               5                   10                  15

Ser Phe Leu Pro Ser Asp Phe Phe Pro Ser Val Arg Asp Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ile Thr Ile Met Arg Ile Lys Pro His Gln Ser Gln His Ile Gly Gly
                85                  90                  95

Ala Thr Ser Arg Asp Leu Val Val Ser Tyr Val Asn Thr Asn Met Gly
            100                 105                 110

Leu Lys Phe Arg Gln Leu Leu Trp Phe His Ile Ser Cys Leu Thr Phe
        115                 120                 125

Gly Arg Glu Thr Val Leu Glu Tyr Leu Val Ser Phe Gly Val Trp Ile
    130                 135                 140

Arg Thr Pro Pro Ala Tyr Arg Pro Pro Asn Ala Pro Ile Leu Ser Thr
145                 150                 155                 160

Leu Pro Glu Thr Thr Val Val Arg Arg Gly Arg Ser Pro Arg Arg
                165                 170                 175

Arg Thr Pro Ser Pro Arg Arg Arg Ser Gln Ser Pro Arg Arg Arg
                180                 185                 190

Arg Ser Gln Ser Arg Glu Ser Gln Cys
        195                 200

<210> SEQ ID NO 29
<211> LENGTH: 627
<212> TYPE: DNA
<213> ORGANISM: Artificial Sequence
<220> FEATURE:
<223> OTHER INFORMATION: Synthetic HBc-hAng2 chimera antigen
<220> FEATURE:
<221> NAME/KEY: CDS
<222> LOCATION: (4)..(618)

<400> SEQUENCE: 29 gcc atg gat atc gat cct tat aaa gaa ttc gga gct act gtg gag tta     48
    Met Asp Ile Asp Pro Tyr Lys Glu Phe Gly Ala Thr Val Glu Leu
    1               5                   10                  15 ctc tcg ttt ctc ccg agt gac ttc ttt cct tca gta cga gat ctt ctg    96
Leu Ser Phe Leu Pro Ser Asp Phe Phe Pro Ser Val Arg Asp Leu Leu
                20                  25                  30 gat acc gcc agc gcg ctg tat cgg gaa gcc ttg gag tct cct gag cac   144
Asp Thr Ala Ser Ala Leu Tyr Arg Glu Ala Leu Glu Ser Pro Glu His
```

|                                                                                      |     |
|--------------------------------------------------------------------------------------|-----|
|                       35                  40                  45                     |     |
| tgc agc cct cac cat act gcc ctc agg caa gca att ctt tgc tgg ggg                      | 192 |
| Cys Ser Pro His His Thr Ala Leu Arg Gln Ala Ile Leu Cys Trp Gly                      |     |
|          50                  55                  60                                  |     |
| gag ctc atg act ctg gcc acg tgg gtg ggt gtt aac ttg gaa gat cca                      | 240 |
| Glu Leu Met Thr Leu Ala Thr Trp Val Gly Val Asn Leu Glu Asp Pro                      |     |
| 65                  70                  75                                           |     |
| gct atc act cca cag agg cag aac aca aat aag ttc aac ggc att aaa                      | 288 |
| Ala Ile Thr Pro Gln Arg Gln Asn Thr Asn Lys Phe Asn Gly Ile Lys                      |     |
| 80                  85                  90                  95                       |     |
| tgg tac tac ggt gct act agc agg gac ctg gta gtc agt tat gtc aac                      | 336 |
| Trp Tyr Tyr Gly Ala Thr Ser Arg Asp Leu Val Val Ser Tyr Val Asn                      |     |
|                 100                 105                 110                          |     |
| act aat atg ggt tta aag ttc agg caa ctc ttg tgg ttt cac att agc                      | 384 |
| Thr Asn Met Gly Leu Lys Phe Arg Gln Leu Leu Trp Phe His Ile Ser                      |     |
|                 115                 120                 125                          |     |
| tgc ctc act ttc ggc cga gaa aca gtt cta gaa tat ttg gtg tct ttc                      | 432 |
| Cys Leu Thr Phe Gly Arg Glu Thr Val Leu Glu Tyr Leu Val Ser Phe                      |     |
|             130                 135                 140                              |     |
| gga gtg tgg atc cgc act cct cca gct tat agg cct ccg aat gcc cct                      | 480 |
| Gly Val Trp Ile Arg Thr Pro Pro Ala Tyr Arg Pro Pro Asn Ala Pro                      |     |
| 145                 150                 155                                          |     |
| atc ctg tcg aca ctc ccg gag act act gtt gtt aga cgt cga ggc agg                      | 528 |
| Ile Leu Ser Thr Leu Pro Glu Thr Thr Val Val Arg Arg Arg Gly Arg                      |     |
| 160                 165                 170                 175                      |     |
| tca cct aga aga aga act cct tcg cct cgc agg cga agg tct caa tcg                      | 576 |
| Ser Pro Arg Arg Arg Thr Pro Ser Pro Arg Arg Arg Ser Gln Ser                          |     |
|                 180                 185                 190                          |     |
| ccg cgg cgc cga aga tct caa tct cgg gaa tct caa tgt tag tgagaggcc                    | 627 |
| Pro Arg Arg Arg Arg Ser Gln Ser Arg Glu Ser Gln Cys                                  |     |
|             195                 200                                                  |     |

<210> SEQ ID NO 30
<211> LENGTH: 204
<212> TYPE: PRT
<213> ORGANISM: Artificial Sequence
<220> FEATURE:
<223> OTHER INFORMATION: Synthetic Construct

<400> SEQUENCE: 30

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ile Thr Pro Gln Arg Gln Asn Thr Asn Lys Phe Asn Gly Ile Lys Trp
                85                  90                  95

Tyr Tyr Gly Ala Thr Ser Arg Asp Leu Val Val Ser Tyr Val Asn Thr
            100                 105                 110

Asn Met Gly Leu Lys Phe Arg Gln Leu Leu Trp Phe His Ile Ser Cys
        115                 120                 125

Leu Thr Phe Gly Arg Glu Thr Val Leu Glu Tyr Leu Val Ser Phe Gly
    130                 135                 140

-continued

```
Val Trp Ile Arg Thr Pro Pro Ala Tyr Arg Pro Pro Asn Ala Pro Ile
145                 150                 155                 160

Leu Ser Thr Leu Pro Glu Thr Thr Val Val Arg Arg Arg Gly Arg Ser
                165                 170                 175

Pro Arg Arg Arg Thr Pro Ser Pro Arg Arg Arg Arg Ser Gln Ser Pro
            180                 185                 190

Arg Arg Arg Arg Ser Gln Ser Arg Glu Ser Gln Cys
            195                 200

<210> SEQ ID NO 31
<211> LENGTH: 7
<212> TYPE: PRT
<213> ORGANISM: Homo sapiens

<400> SEQUENCE: 31

Met Arg Ile Lys Pro His Gln
1               5

<210> SEQ ID NO 32
<211> LENGTH: 17
<212> TYPE: PRT
<213> ORGANISM: Mus musculus

<400> SEQUENCE: 32

Met Gln Ile Met Arg Ile Lys Pro His Gln Ser Gln His Ile Gly Glu
1               5                   10                  15

Met

<210> SEQ ID NO 33
<211> LENGTH: 17
<212> TYPE: PRT
<213> ORGANISM: Homo sapiens

<400> SEQUENCE: 33

Met Gln Ile Met Arg Ile Lys Pro His Gln Gly Gln His Ile Gly Glu
1               5                   10                  15

Met
```

DNA VACCINE CONTAINING VEGF-SPECIFIC EPITOPE AND/OR ANGIOPOIETIN-2-SPECIFIC EPITOPE

CROSS-REFERENCE TO RELATED APPLICATIONS

This patent application is the U.S. national phase of International Patent Application No. PCT/JP2013/073045, filed Aug. 28, 2013, which claims the benefit of Japanese Patent Application No. 2012-191717, filed on Aug. 31, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 57,588 bytes ASCII (Text) file named "719932SequenceListing.txt," created Feb. 27, 2015.

TECHNICAL FIELD

The present invention relates to a DNA vaccine effective for the treatment or prophylaxis of cancer.

BACKGROUND ART

For a tumor to grow large, blood vessels to deliver nutrition and oxygen to the tumor need to be increased depending on the growth of the tumor. Tumor cells are considered to induce angiogenesis of tumor blood vessels by secreting the vascular growth factor by themselves that stimulate the growth of vascular endothelial cells of neighboring blood vessels. Therefore, attempts have been made to treat or prevent tumor by inhibiting the function of vascular growth factors and suppressing tumor angiogenesis. As one of such methods, a vaccine therapy targeting tumor angiogenesis-related factors has been attracting attention. In the vaccine therapy, cancer is treated or prevented by administering a tumor angiogenesis-related factor, an epitope contained in the factor, or an expression vector encoding them to cancer patients or targets having a risk of developing cancer to induce an antibody against the tumor angiogenesis-related factor in the body of the patients, thereby neutralizing the function of the factor and suppressing tumor angiogenesis. As the tumor angiogenesis-related factor, various factors such as VEGF, angiopoietin, FGF, PDGF and the like are known.

For example, patent document 1 discloses a method of inhibiting vascular endothelial cell proliferation in a tumor microenvironment, preventing angiogenesis and inhibiting growth and metastasis of tumor, by administering a DNA vaccine encoding VEGF receptor-1, VEGF receptor-2 or Flk-1.

Patent document 2 describes suppression of angiogenesis-related diseases, particularly of the development and metastasis of cancer, by using heterologous VEGF vaccines.

However, the immune tolerance to factors such as VEGF and the like has generally been established since these factors are the patient's self components. Therefore, even when these factors or partial peptides thereof are directly administered to patients, it is difficult to efficiently induce antibodies to these factors in the body of the patients. As such, some technical idea is necessary to make the patients' immune system recognize these self-antigens, thereby inducing the production of the antibodies thereto.

Hepatitis B virus core (HBc) antigen protein constitutes spherical core particles by self-assembly. The core particles have very high immunogenicity. When a fusion polypeptide obtained by inserting a desired epitope into a particular site of the HBc antigen protein, or connecting a desired epitope to the terminus of the HBc antigen protein is used, the epitope is presented on the surface of the particles formed by self-assembly. Using the fusion polypeptide, the inserted epitope is easily recognized by the immune system, and the production of the antibody that recognizes the epitope can be efficiently induced. Therefore, utilizing the HBc antigen protein as a platform of vaccine, attempts have been made to induce production of the antibody even though an antigen is difficult to be recognized by the immune system (non-patent document 1, non-patent document 2).

Patent document 3 discloses particles composed of a chimeric HBc antigen protein containing an exogenous amino acid sequence having an epitope, wherein the exogenous amino acid sequence is inserted between the amino acid residues 80-81 of the HBc antigen.

However, the effectiveness of the vaccine for tumor angiogenesis-related factor is not sufficiently satisfactory.

DOCUMENT LIST

Patent Documents patent document 1: JP-A-2005-519092
patent document 2: Chinese patent publication No. 1406629
patent document 3: JP-B-3228737

Non-Patent Documents non-patent document 1: D. C. Whitacre et al., Expert Rev. Vaccines, vol. 8, no. 11, pp. 1565-1573, 2009
non-patent document 2: B. E. Clarke et al., Nature, vol. 330, pp. 381-384, 1987

SUMMARY OF THE INVENTION

Problems to be Solved by the Invention

As described in patent document 1, when VEGF receptor is used as a vaccine antigen, since the target to be attacked by vaccine becomes a vascular endothelial cell or a part of cancer cells expressing the VEGF receptor, an antitumor effect is exhibited by suppressing the angiogenesis in the tumor by enhancing cytotoxic immunity. However, since VEGF receptor is expressed not only in neovascular endothelial cells of tumor tissues but also normal vascular endothelial cells, when VEGF receptor is used as a vaccine antigen, an adverse influence may be exerted on the normal blood vessel function.

Accordingly, the present invention aims to provide a superior vaccine for the treatment or prophylaxis of cancer, which targets a tumor angiogenesis-related factor and has a reduced risk of an adverse influence on the normal blood vessel function.

Means of Solving the Problems

The present inventors have conducted intensive studies and found that administration of an expression vector of chimeric hepatitis B virus core antigen polypeptide obtained by inserting a specific epitope of humoral factors such as VEGF and angiopoietin-2 between the amino acid residues 80 and 81 of hepatitis B virus core antigen polypeptide predominately induces humoral immunity to the humoral factors, and enables treatment or prophylaxis of cancer by effectively suppressing tumor angiogenesis while avoiding an adverse influence on the normal blood vessel function by the cell-mediated immunity. Based on these findings, they have further studied and completed the present invention.

That is, the present invention relates to the following.

[1] A therapeutic or prophylactic agent for cancer, comprising an expression vector encoding a chimeric Hepatitis B virus core antigen polypeptide inserted with an amino acid sequence comprising a specific epitope of VEGF and/or a specific epitope of angiopoietin-2, wherein the amino acid sequence comprising the specific epitope is inserted between the amino acid residues 80 and 81 of the hepatitis B virus core antigen polypeptide.

[2] The therapeutic or prophylactic agent of [1], wherein the cancer is a solid tumor.

[3] The therapeutic or prophylactic agent of [1] or [2], wherein the solid tumor is any one kind selected from the group consisting of non-small cell lung cancer, colorectal cancer, breast cancer, pancreatic cancer, gastric cancer, uterine cancer and prostate cancer.

[4] The therapeutic or prophylactic agent of any of [1]-[3], wherein the inserted amino acid sequence comprises the amino acid sequence shown in SEQ ID NO: 1 or 2.

[5] The therapeutic or prophylactic agent of any of [1]-[3], wherein the inserted amino acid sequence comprises the amino acid sequence shown in SEQ ID NO: 31, 32 or 33, a partial sequence of the amino acid sequence shown in SEQ ID NO: 32, which comprises the amino acid sequence shown in SEQ ID NO: 1 or 31, or
a partial sequence of the amino acid sequence shown in SEQ ID NO: 33, which comprises the amino acid sequence shown in SEQ ID NO: 2 or 31.

[6] The therapeutic or prophylactic agent of any of [1]-[3], wherein the inserted amino acid sequence comprises the amino acid sequence shown in SEQ ID NO: 3 or 4.

[7] The therapeutic or prophylactic agent of any of [1]-[6], wherein the inserted amino acid sequence further comprises one or more specific epitopes.

[8] The therapeutic or prophylactic agent of any one of [1]-[7], which is administered plural times.

[9] The therapeutic or prophylactic agent of [8], wherein the administration number is 2, 3 or 4.

[10] The therapeutic or prophylactic agent of [9], wherein the administration number is 3.

[11] The therapeutic or prophylactic agent of any one of [1]-[10], which is administered 3 times at half year intervals.

[12] An expression vector encoding a chimeric Hepatitis B virus core antigen polypeptide inserted with an amino acid sequence comprising a specific epitope of VEGF and/or a specific epitope of angiopoietin-2, which is for use in the treatment or prophylaxis of cancer, wherein the amino acid sequence comprising the specific epitope is inserted between the amino acid residues 80 and 81 of the hepatitis B virus core antigen polypeptide.

[13] An expression vector encoding a chimeric Hepatitis B virus core antigen polypeptide inserted with amino acid sequence containing the amino acid sequence shown by SEQ ID NO: 1 or 2, which is for use in the treatment or prophylaxis of non-small cell lung cancer, colorectal cancer, breast cancer, pancreatic cancer, gastric cancer, uterine cancer or prostate cancer, wherein the amino acid sequence is inserted between the amino acid residues 80 and 81 of the hepatitis B virus core antigen polypeptide.

[14] An expression vector encoding a chimeric Hepatitis B virus core antigen polypeptide inserted with amino acid sequence containing the amino acid sequence shown by SEQ ID NO: 3 or 4, which is for use in the treatment or improvement of non-small cell lung cancer, colorectal cancer, breast cancer, pancreatic cancer, gastric cancer, uterine cancer or prostate cancer, wherein the amino acid sequence is inserted between the amino acid residues 80 and 81 of the hepatitis B virus core antigen polypeptide.

[15] The expression vector of any of [12]-[14], wherein the inserted amino acid sequence further comprises one or more specific epitopes.

[16] A method for the treatment or prophylaxis of cancer in a mammal, comprising administering an effective amount of an expression vector encoding a chimeric Hepatitis B virus core antigen polypeptide inserted with an amino acid sequence comprising a specific epitope of VEGF and/or a specific epitope of angiopoietin-2 to the mammal, wherein the amino acid sequence comprising the specific epitope is inserted between the amino acid residues 80 and 81 of the hepatitis B virus core antigen polypeptide.

Effect of the Invention

The present invention provides a superior vaccine for the treatment or prophylaxis of cancer, which targets a tumor angiogenesis-related factor and has a reduced risk of an adverse influence on the normal blood vessel function.

Since the vaccine of the present invention predominately induces humoral immunity to humoral factors such as VEGF and angiopoietin-2, rather than the cell-mediated immunity, a risk of an adverse influence of the cell-mediated immunity on the normal blood vessel function can be reduced.

Moreover, since VEGF and angiopoietin-2 are secreted proteins, tissue inflammation is not easily developed, since an antibody induced by vaccination mainly binds to the secreted proteins in blood.

BRIEF DESCRIPTION OF THE DRAWINGS

FIG. 1 shows the effect of vaccination on the growth of tumor tissues. The vertical axis shows the volume of tumor tissues, and the horizontal axis shows the days after tumor injection.

FIG. 2 shows the effect of vaccination on the survival rate of mice injected with tumor. The vertical axis shows the survival rate and the horizontal axis shows the days after tumor injection.

FIG. 3 shows framework residues at VEGF-bevacizumab interface. Red: residues in binding surface with bevacizumab. Yellow: especially important residues of Red. Blue: residues in binding surface with VEGFR-1. Green, residues in binding surface with VEGFR-2. Each residue is represented by single-letter codes.

FIG. 4 shows time course of DNA vaccination. Vaccination was initially performed using 6 week-old mice (0 w), and subsequent vaccinations were given at 2, 4 and 8 weeks after first vaccination.

FIG. 5 shows titers of anti-VEGF antibodies at 16 weeks. Total IgG titers for VEGF were quantified in mouse sera (100 dilution) from mice immunized with HBc-mVEGF (7 a.a.), HBc-mVEGF (13 a.a.), HBc-mVEGF (17 a.a.) or HBc, respectively. Data were means±S.E.M.

FIG. 6 shows plasmid DNA construction of the vaccine. Plasmid maps of pcDNA3.1-HBc (control vector) and pcDNA3.1-HBc-mVEGF (13 a.a.) (vaccination vector) are illustrated. HBc indicates the full sequence of HBc, HBc-N indicates the N-terminus of HBc (1-80 a.a.), and HBc-C indicates the C-terminus of HBc (81-183 a.a.). mVEGF 13 a.a. indicates the antigen for the mouse VEGF protein. Detail information regarding the VEGF vaccine plasmid design is shown below the plasmid maps. Thirteen amino acids (IMRIKPHQSQHIGE) (SEQ ID NO: 1), which served as an antigen for VEGF and the linkers (the N-terminal I-T dipeptide linkers and C-terminal GAT tripeptide), were designed fuse in-frame to VEGF to allow for flexibility in the conformation of the VEGF epitope when the surface is exposed on the HBc particle. The VEGF 13 a.a. and linkers are represented by single-letter codes.

Figure 7:
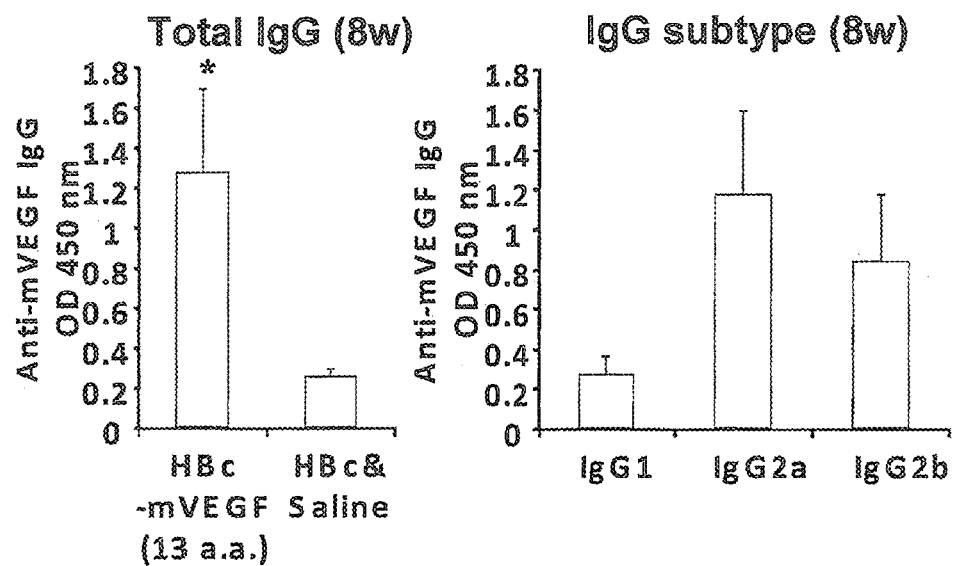

FIG. 7 shows titers of anti-VEGF antibodies at 8 weeks. Total IgG titers for VEGF were increased only in mouse sera (100 dilution) from the HBc-mVEGF (13 a.a.) group (left panel). The IgG subtype distribution (IgG1, IgG2a or IgG2b) was also evaluated using subtype-specific IgG antibodies in mouse sera (100 dilution) from the HBc-VEGF (13a.a.) group (right panel). Data were means±S.E.M. *p<0.05 versus control (HBc and Saline).

Figure 8:
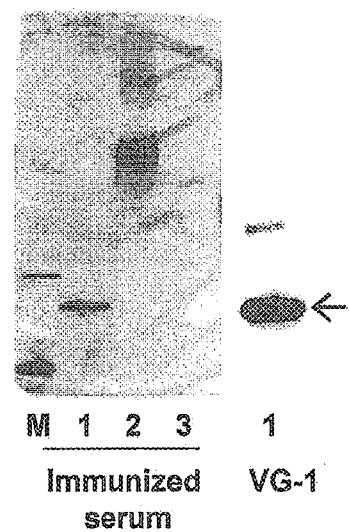

FIG. 8 shows specific binding of immunized serum to VEGF. Immunized serum used as primary antibody in western blot bound to not only BSA-conjugated mVEGF (13 a.a.) but recombinant mouse VEGF (rmVEGF). Loading samples were as follows. Lane 1: recombinant mouse VEGF-A. Lane 2: BSA-conjugated mVEGF (13 a.a.). Lane 3: BSA-conjugated human Angiopoietin-2 peptide as negative protein. VG-1, commercial monoclonal antibody against VEGF, was used as positive antibody.

Figure 9:
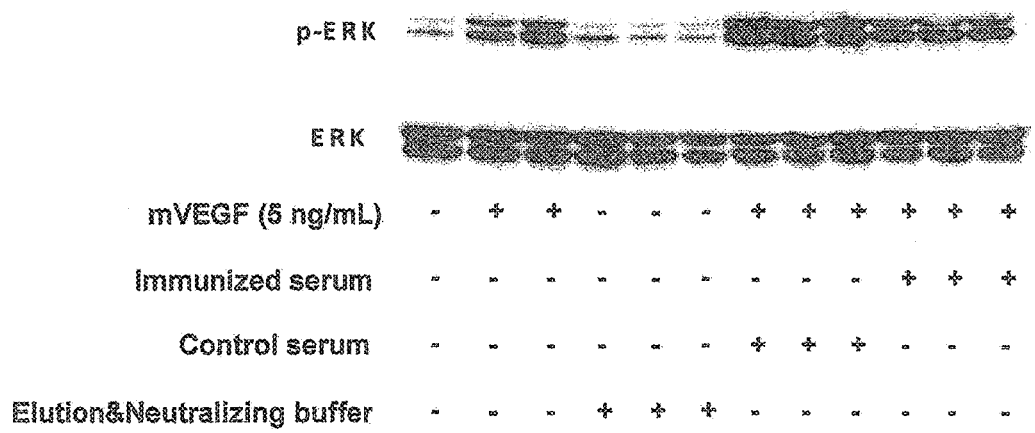

FIG. 9 shows Western blot analysis of cell lysates from HUVECs stimulated for 10 min with mVEGF at 5 ng/mL in the presence of immunized serum or control serum for p-ERK and total ERK.

Figure 10:
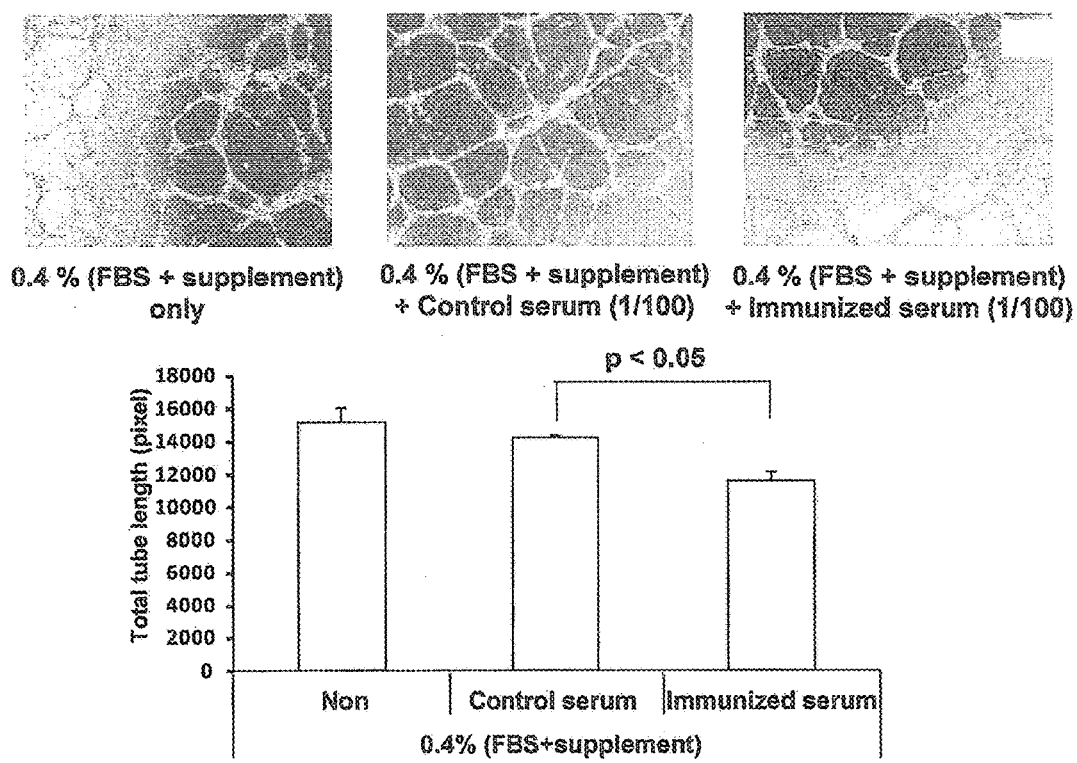

FIG. 10 shows effects of immunized serum on VEGF-induced tube formation of HUVECs. HUVECs were plated on matrigel-coated plates at density of $1\times10^5$ cells/well and incubated in the presence of control serum or immunized serum. After 7 hours, capillary network were photographed and quantified. Representative endothelial tubes were shown. Magnification: 50×.

Data were means±S.E.M. of triplicates.

DESCRIPTION OF EMBODIMENTS

The present invention provides a therapeutic or prophylactic agent for cancer, comprising an expression vector encoding a chimeric hepatitis B virus core antigen polypeptide inserted with an amino acid sequence comprising a specific epitope of VEGF and/or a specific epitope of angiopoietin-2, wherein the amino acid sequence comprising the specific epitope is inserted between the amino acid residues 80 and 81 of the hepatitis B virus core antigen polypeptide.

When an expression vector encoding a chimeric hepatitis B virus core antigen polypeptide inserted with an amino acid sequence containing a specific epitope of VEGF and/or a specific epitope of angiopoietin-2 is administered, an immune response (preferably humoral immune response such as antibody production and the like) to the specific epitope of VEGF and/or the specific epitope of angiopoietin-2 in the expressed chimeric hepatitis B virus core antigen polypeptide is induced, and the activity of VEGF and/or angiopoietin-2 is neutralized with the antibody, whereby the angiogenesis around the cancer tissues can be suppressed and the growth of the cancer tissue can be inhibited. Accordingly, the cancer to be the target of the therapeutic or prophylactic agent of the present invention is preferably a solid tumor. Examples of the solid tumor include, but are not limited to, non-small cell lung cancer, colorectal cancer, breast cancer, pancreatic cancer, gastric cancer, uterine cancer, prostate cancer and the like.

While the cancer to be the target of the therapeutic or prophylactic agent of the present invention is not limited, it is preferably a cancer expressing VEGF and/or angiopoietin-2. The presence or absence of expression of VEGF and/or angiopoietin-2 in cancer can be confirmed by immunological methods (immunohistochemical staining, Western blotting etc.) using a specific antibody to VEGF and/a specific antibody to angiopoietin-2.

While use of VEGF and angiopoietin-2 derived from a mammal of the application target of the therapeutic or prophylactic agent of the present invention is intended in the present invention, it is not limited thereto. The application target of the therapeutic or prophylactic agent of the present invention is a mammal. Examples of the mammal include rodents such as mouse, rat, hamster, guinea pig and the like, lagomorphas such as rabbit and the like, ungulates such as swine, bovine, goat, horse, sheep and the like, carnivore such as dog, cat and the like, primates such as human, monkey, *Macaca mulatta*, *Macaca fascicularis*, marmoset, orangutan, chimpanzee and the like, and the like. The mammal is preferably a rodent (mouse etc.) or a primate (human etc.). Therefore, for example, when the therapeutic or prophylactic agent of the present invention is applied to human, use of VEGF and angiopoietin-2 derived from the human is intended, but is not limited thereto. Also, the therapeutic or prophylactic agent of the present invention is applied to mouse, use of VEGF and angiopoietin-2 derived from the mouse is intended, but is not limited thereto.

In the present specification, regarding the particular factor X (polypeptide or polynucleotide), "factor X derived from organism Y" or "organism Y factor X" means that the amino acid sequence or nucleic acid sequence of factor X has the same or substantially the same amino acid sequence or nucleic acid sequence as the amino acid sequence or nucleic acid sequence of factor X naturally expressed in organism Y. Being "substantially the same" means that the amino acid sequence or nucleic acid sequence of interest has not less than 70% (preferably not less than 80%, more preferably not less than 90%, still more preferably not less than 95%, most preferably not less than 99%) identity with the amino acid sequence or nucleic acid sequence of factor X naturally expressed in organism Y, and the function of factor X is maintained.

VEGF and angiopoietin-2 are known angiogenesis factors, and the amino acid sequences and cDNA sequences thereof are also known. VEGF contains 7 subtypes including A, B, C, D, E, PLGF-1 and PLGF-2, and a specific epitope of VEGF of any subtype can be used in the present invention as long as it treats or prevents cancer. Preferably, specific epitopes of VEGF-A, B, C, D, E are used. Representative amino acid sequences include the following and the like.

TABLE 1

| | Human | Mouse |
| --- | --- | --- |
| VEGF-A | P15692 (SEQ ID NO: 13) | Q00731 (SEQ ID NO: 19) |
| VEGF-B | P49765 (SEQ ID NO: 14) | P49766 (SEQ ID NO: 20) |
| VEGF-C | P49767 (SEQ ID NO: 15) | P97953 (SEQ ID NO: 21) |
| VEGF-D | O43915 (SEQ ID NO: 16) | P97946 (SEQ ID NO: 22) |
| VEGF-E | Q9NRA1 (SEQ ID NO: 17) | Q8CI19 (SEQ ID NO: 23) |
| PLGF-1 | P49763 (SEQ ID NO: 18) | P49764 (SEQ ID NO: 24) |

Representative amino acid sequences of angiopoietin-2 are as follows.

TABLE 2

| | Human | Mouse |
|---|---|---|
| Angiopoietin-2 | O15123 (SEQ ID NO: 25) | O35608 (SEQ ID NO: 26) |

In the present specification, "epitope" refers to a basic element or minimum unit for recognition by each antibody or T cell receptor, which is a particular domain, region or molecular structure the aforementioned antibody or T cell receptor binds to.

An epitope of VEGF and an epitope of angiopoietin-2 to be used in the present invention are specific to said VEGF and angiopoietin-2. Being "specific" means that the gene products (excluding variable regions of immunoglobulin and T cell receptor) other than the VEGF and angiopoietin-2 naturally expressed in a mammal, from which the VEGF and angiopoietin-2 derive, do not contain said epitope.

As the specific epitope of VEGF and specific epitope of angiopoietin-2 to be used in the present invention, one at a position where the activity of VEGF and angiopoietin-2 is inhibited when an antibody that recognizes the epitope binds to the epitope, is preferably selected. Such epitope can be in a functional site, for example, receptor binding site, divalent ion binding site, site recognized by a specific enzyme and the like. An epitope contained in a site removed during the maturation process of VEGF and angiopoietin-2, such as signal sequence and the like, is preferably excluded from epitope to be used in the present invention. Those of ordinary skill in the art can appropriately select the epitope based on the steric structures and the like of VEGF and angiopoietin-2.

The length of the amino acid sequence of the epitope is generally 5-30 amino acids, preferably 6-25 amino acids, more preferably 10-18 amino acids, furthermore preferably 11-16 amino acids. When the amino acid sequence is too short, the antigenicity of the epitope may be lost. When the amino acid sequence is too long, chimeric hepatitis B virus core antigen polypeptide does not easily form core particles due to self-assembly, as a result of which an antibody that specifically recognizes the epitope may not be produced, and a superior treatment or improvement effect on cancer may not be obtained.

Specific examples of a preferable epitope of VEGF and angiopoietin-2 include the following.

```
(VEGF)
(i)      IMRIKPHQGQHIG       (SEQ ID NO:  1)

(ii)     IMRIKPHQGQHIG       (SEQ ID NO:  2)

(angiopoietin-2)
(iii)    PQRQNTNKFNGIKWYY    (SEQ ID NO:  3)

(iv)     YYPQRQNTNKE         (SEQ ID NO:  4)
```

In a further aspect, specific preferable examples of VEGF include the following.

```
(v)      MRIKPHQ             (SEQ ID NO: 31)

(vi)     MQIMRIKPHQSQHIGEM   (SEQ ID NO: 32)

(vii)    MQIMRIKPHQSQHIGEM   (SEQ ID NO: 33)
```

(viii) an epitope consisting of a partial sequence of the amino acid sequence shown in SEQ ID NO: 32, which contains the amino acid sequence shown in SEQ ID NO: 1 or 31
(ix) an epitope consisting of a partial sequence of the amino acid sequence shown in SEQ ID NO: 33, which contains the amino acid sequence shown in SEQ ID NO: 2 or 31

SEQ ID NOs: 1, 31 and 32 are partial amino acid sequences of mouse VEGF-A. SEQ ID NOs: 2, 31 and 34 are partial amino acid sequences of human VEGF-A. SEQ ID NOs: 3 and 4 are partial amino acid sequences of human angiopoietin-2.

The length of the partial sequence in the above-mentioned (viii) and (ix) is 8, 9, 10, 11, 12, 13, 14, 15 or 16 amino acids.

Hepatitis B virus core antigen polypeptide used in the present invention is
(1) a polypeptide containing the amino acid sequence shown by SEQ ID NO: 6, or
(2) a polypeptide containing an amino acid sequence having not less than 90% (preferably not less than 95%, more preferably not less than 97%, still more preferably not less than 99%) identity with the amino acid sequence shown by SEQ ID NO: 6, and having an activity to form core particles due to self-assembly.

Self-assembly refers to a phenomenon wherein molecules dissolved in a solution associate to form an assembly. Core particle refers to a rigid structure having a specific repetitive constitution. In the present specification, the core particle may be a product of synthesis steps or a product of biological steps.

As the polypeptide of the embodiment of (2), a polypeptide containing the amino acid sequence shown by SEQ ID NO: 7 disclosed in WO 2003/031466 can be mentioned. A polypeptide containing the amino acid sequence shown by SEQ ID NO: 7 except that one or plural cysteine residues of the positions 48, 61, 107 and 185 are deleted or substituted by other amino acid residue (e.g., serine residue) is also preferable as the polypeptide of the embodiment of (2). As recognized by those of ordinary skill in the art, in a polypeptide having an amino acid sequence different from that of SEQ ID NO: 7, cysteine residues at similar positions can be deleted or substituted by other amino acid residues, and polypeptides obtained by such deletion and substitution are also encompassed in the polypeptide of the embodiment of (2).

The polypeptide of the embodiment of (2) also encompasses a variant polypeptide wherein the isoleucine residue at the position corresponding to the position 97 of SEQ ID NO: 7 is substituted by leucine residue or phenylalanine residue (Yuan et al., J. Virol. vol. 73, pages 10122-10128 (1999)). In addition, amino acid sequences of many HBcAg variants and several kinds of hepatitis B core antigen precursor variants are disclosed in GenBank reports AAF121240, AF121239, X85297, X02496, X85305, X85303, AF151735, X85259, X85286, X85260, X85317, X85298, AF043593, M20706, X85295, X80925, X85284, X85275, X72702, X85291, X65258, X85302, M32138, X85293, X85315, U95551, X85256, X85316, X85296, AB033559, X59795, X8529, X85307, X65257, X85311, X85301, X85314, X85287, X85272, X85319, AB010289, X85285, AB010289, AF121242, M90520, P03153, AF110999 and M95589 (each of the disclosures is incorporated in the present specification by reference), and polypeptides containing amino acid sequences of these variants are also encompassed in the polypeptide of the embodiment of (2). The above-mentioned variants have amino acid sequences different at many positions including amino acid residues corresponding to the amino acid residues present at the positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO: 7.

Furthermore, polypeptides containing the amino acid sequences of the HBcAg variants described in WO 01/98333, WO 01/77158 and WO 02/14478, all of which are incorporated in the present specification by reference are also encompassed in the polypeptide of the embodiment of (2).

In the present specification, unless particularly indicated, the positions of amino acid residues in the amino acid sequence of hepatitis B virus core antigen polypeptide are specified with the amino acid sequence shown by SEQ ID NO: 6 as the standard. When a polypeptide does not contain the amino acid sequence shown by SEQ ID NO: 6, the amino acid sequence of the polypeptide is aligned with the amino acid sequence shown by SEQ ID NO: 6, and the position of the corresponding amino acid residue is adopted.

The hepatitis B virus core antigen polypeptide used in the present invention is preferably a polypeptide containing the amino acid sequence shown by SEQ ID NO: 6.

In the chimeric hepatitis B virus core antigen polypeptide to be used in the present invention, an amino acid sequence comprising a specific epitope of VEGF and/or a specific epitope of angiopoietin-2 is inserted between the amino acid residues 80 and 81 of the hepatitis B virus core antigen polypeptide. That is, the chimeric hepatitis B virus core antigen polypeptide to be used in the present invention contains the following elements (a)-(c):
(a) N-terminus part polypeptide residues of hepatitis B virus core antigen polypeptide (consisting of the continuous partial amino acid sequence of hepatitis B virus core antigen polypeptide from N-terminus to the amino acid residue 80),
(b) an amino acid sequence consisting of a specific epitope of VEGF and/or a specific epitope of angiopoietin-2, and
(c) C-terminus partial polypeptide residues of hepatitis B virus core antigen polypeptide (consisting of the continuous partial amino acid sequence of hepatitis B virus core antigen polypeptide from the amino acid residue 81 to C-terminus) in the order of (a), (b), (c) from the N terminus side.

The chimeric hepatitis B virus core antigen polypeptide to be used in the present invention having the above-mentioned constitution forms core particles due to self-assembly, and a specific epitope of VEGF and/or a specific epitope of angiopoietin-2 is presented on the outside of the particles.

The amino acid sequence inserted between constituent element (a) and constituent element (c) may further contain, in addition to constituent element (b) (amino acid sequence consisting of a specific epitope of VEGF and/or a specific epitope of angiopoietin-2), one or more (preferably 1-3, more preferably 1) specific epitopes. The further specific epitope may be inserted at any position between constituent element (a) and constituent element (b), or constituent element (b) and constituent element (c). The length of the amino acid sequence of the further specific epitope is generally 5-30 amino acids, preferably 6-25 amino acids, more preferably 10-18 amino acids, further more preferably 11-16 amino acids.

When plural specific epitopes are inserted between constituent element (a) and constituent element (c), the specific epitopes may be directly linked by a covalent bond, or linked via a spacer sequence. The spacer sequence means an amino acid sequence containing one or more amino acid residues to be inserted between two adjacent constituent elements contained in the chimeric hepatitis B virus core antigen polypeptide. The specific epitopes are preferably linked via a spacer sequence so that plural specific epitopes can be stably presented while maintaining their structures. The length of the spacer sequence is not limited as long as the chimeric hepatitis B virus core antigen polypeptide forms core particles by self-assembly, and all inserted specific epitopes are presented outside the particles, and is generally 1-10 amino acids, preferably 1-5 amino acids, more preferably 1-3 amino acids, most preferably 2 or 3 amino acids.

A specific epitope on the most N-terminal side between constituent element (a) and constituent element (c), and constituent element (a) may be directly connected by a covalent bond or via a spacer sequence. The element (a) and the specific epitope on the most N-terminal side are preferably connected via a spacer sequence so that a specific epitope of VEGF and/or a specific epitope of angiopoietin-2 will be stably presented on the outside of the particles formed by self-assembly of chimeric hepatitis B virus core antigen polypeptides, while maintaining its structure. While the length of the spacer sequence is not limited as long as chimeric hepatitis B virus core antigen polypeptide forms core particles due to self-assembly and a specific epitope of VEGF and/or a specific epitope of angiopoietin-2 is presented on the outside of the particles, it is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms core particles due to self-assembly and a specific epitope of VEGF and/or a specific epitope of angiopoietin-2 is presented on the outside of the particles. Examples of a preferable spacer sequence include, but are not limited to, IT, GAT, CGG and the like.

A specific epitope on the most C-terminal side between constituent element (a) and constituent element (c), and constituent element (c) may be directly connected by a covalent bond or via a spacer sequence. The element (b) and the element (c) are preferably connected via a spacer sequence so that a specific epitope of VEGF and/or a specific epitope of angiopoietin-2 will be stably presented on the outside of the particles formed by self-assembly of chimeric hepatitis B virus core antigen polypeptides, while maintaining its structure. While the length of the spacer sequence is not limited as long as chimeric hepatitis B virus core antigen polypeptide forms core particles due to self-assembly and a specific epitope of VEGF and/or a specific epitope of angiopoietin-2 is presented on the outside of the particles, it is generally 1-10 amino acids, preferably 1-5 amino acids, more preferably 1-3 amino acids, most preferably 2 or 3 amino acids. Also, the kind of the spacer sequence is not limited as long as chimeric hepatitis B virus core antigen polypeptide forms core particles due to self-assembly and a specific epitope of VEGF and/or a specific epitope of angiopoietin-2 is presented on the outside of the particles. Examples of a preferable spacer sequence include, but are not limited to, IT, GAT, CGG and the like.

The length of the amino acid sequence inserted between constituent element (a) and constituent element (c) is not particularly limited as long as chimeric hepatitis B virus core antigen polypeptide forms core particles due to self-assembly, and a VEGF specific epitope and/or a angiopoietin-2 specific epitope is presented on the outside of the particles, and cancer can be treated or prevented, and is generally 5-80 amino acids. When the inserted amino acid sequence is too short, the antigenicity as an epitope may be lost. When the inserted amino acid sequence is too long, formation of core particles by chimeric hepatitis B virus core antigen polypeptide due to self-assembly becomes difficult, as a result of which an antibody specifically recognizing the inserted epitope is not produced, and a good treatment or improvement effect on cancer may not be obtained.

The expression vector used in the present invention is a recombinant vector incorporating a polynucleotide encoding the above-mentioned chimeric hepatitis B virus core antigen polypeptide. When the expression vector is administered to a target mammal, the expression vector is intracellularly incorporated into the target mammal, and the cell expresses the above-mentioned chimeric hepatitis B virus core antigen polypeptide. Examples of the expression vector inserted with polynucleotide encoding chimeric hepatitis B virus core antigen polypeptide include plasmid, virus, phage, cosmid and other vectors conventionally used in the art. Examples of the plasmid vector include, but are not limited to, pCAGGS (Gene 108: 193-199 (1991)), pCR-X8 (Vaccine 24: 4942-4950 (2006)), pcDNA3.1 (trade name, Invitrogen), pZeoSV (trade name, Invitrogen), pBK-CMV (trade name, Stratagene) and the like. The virus vector is a DNA virus or an RNA virus. Examples of the virus vector include, but are not limited to, detoxicated retrovirus, adenovirus, adeno-associated virus, herpes virus, vaccinia virus, poxvirus, polio virus, Sindbis virus, Hemagglutinating Virus of Japan (HVJ), SV40, human immunodeficient virus (HIV) and the like. Furthermore, Hemagglutinating Virus of Japan envelope (HVJ-E) and the like can also be utilized.

In the above-mentioned expression vector, polynucleotide (preferably DNA) encoding chimeric hepatitis B virus core antigen polypeptide is operably connected to a promoter capable of exhibiting a promoter activity in the cell of a mammal (preferably human) to be the administration subject.

The promoter to be used is not particularly limited as long as it can function in the cell of a mammal (preferably human) to be the administration subject. Examples of the promoter include pol I promoter, pol II promoter, pol III promoter and the like. Specifically, virus promoters such as SV40-derived initial promoter, cytomegalovirus LTR and the like, mammal constituting protein gene promoters such as β-actin gene promoter and the like, RNA promoters such as tRNA promoter and the like, and the like are used.

The above-mentioned expression vector preferably contains a transcription termination signal, i.e., terminator region, at the downstream of the polynucleotide encoding chimeric hepatitis B virus core antigen polypeptide. It can further contain a selection marker gene for the selection of a transformed cell (gene conferring resistance to medicaments such as tetracycline, ampicillin, kanamycin and the like, gene complementing auxotrophic mutation etc.).

In one embodiment, the above-mentioned expression vector may contain an immune stimulatory sequence (ISS) (also referred to as CpG) to potentiate the immune effect. The immune stimulatory sequence is a DNA containing a non-methylated CpG motif of bacterium, and is known to function as a ligand of a particular receptor (Toll-like receptor 9) (see Biochim. Biophys. Acta 1489, 107-116 (1999) and Curr. Opin. Microbiol. 6, 472-477 (2003) for the detail). Preferable examples of the immune stimulatory sequence include the following.

CpG-B1018 22 bp
(SEQ ID NO: 8)
5'-tga ctg tga acg ttc gag atg a-3'

CpG-A D19 20 bp (D type)
(SEQ ID NO: 9)
5'-ggt gca tcg atg cag ggg gg-3'

CpG-CC274 21 bp
(SEQ ID NO: 10)
5'-tcg tcg aac gtt cga gat gat-3'

CpG-CC695 25 bp
(SEQ ID NO: 11)
5'-tcg aac gtt cga acg ttc gaa cgt t-3'

Alternatively, 2, 3 or 4 from these ISSs may be connected and used. Preferable examples of the connected ISS sequence include the following.

(SEQ ID NO: 12)
5'-ggt gca tcg atg cag ggg gg tga ctg tga acg ttc gag atg a tcg tcg aac gtt cgagat gat tcg aac gtt cga acg ttc gaa cgt t-3'

Those of ordinary skill in the art can construct the aforementioned expression vector according to well-known genetic engineering techniques described in, for example, "edit. Sambrook et al., Molecular Cloning A Laboratory Manual Cold Spring Harbor Laboratory (1989) N.Y.", "edit. Ausubel et al., Current Protocols in Molecular Biology (1987) John Wiley & Sons" and the like.

The therapeutic or improving agent of the present invention can be provided as a pharmaceutical composition containing, in addition to a therapeutically effective amount of the above-mentioned expression vector, any carrier, for example, a pharmaceutically acceptable carrier.

Examples of the pharmaceutically acceptable carrier include, though not limited thereto, excipients such as sucrose, starch, mannit, sorbit, lactose, glucose, cellulose, talc, calcium phosphate, calcium carbonate and the like, binders such as cellulose, methylcellulose, hydroxypropylcellulose, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatics such as citric acid, menthol, glycyrrhizin.ammonium salt, glycine, orange power and the like, preservatives such as sodium benzoate, sodium bisulfite, methylparaben, propylparaben and the like, stabilizers such as citric acid, sodium citrate, acetic acid and the like, suspending agent such as methylcellulose, polyvinylpyrrolidone, aluminum stearate and the like, dispersing agents such as surfactant and the like, diluents such as water, saline and the like, base waxes such as cacao butter, polyethylene glycol, white kerosine and the like, and the like.

The therapeutic or improving agent of the present invention may further contain an adjuvant to potentiate its effect. Examples of the adjuvant include aluminum hydroxide, complete Freund's adjuvant, incomplete Freund's adjuvant, pertussis adjuvant, poly(I:C), CpG-DNA and the like.

To promote intracellular introduction of an expression vector, the therapeutic or prophylactic agent of the present invention may further contain a reagent for nucleic acid introduction. As the reagent for nucleic acid introduction, cationic lipids such as lipofectin (trade name, Invitrogen), lipofectamine (trade name, Invitrogen), transfectam (trade name, Promega), DOTAP (trade name, Roche Applied Science), dioctadecylamidoglycyl spermine (DOGS), L-dioleoyl phosphatidyl-ethanolamine (DOPE), dimethyldioctadecyl-ammonium bromide (DDRB), N,N-di-n-hexadecyl-N,N-dihydroxyethylammonium bromide (DHDEAB), N-n-hexadecyl-N,N-dihydroxyethylammonium bromide (HDEAB), polybrene, poly(ethyleneimine) (PEI) and the like can be used. In addition, an expression vector may be included in any known liposome constituted of a lipid bilayer such as electrostatic liposome. Such liposome may be fused with a virus such as inactivated Hemagglutinating Virus of Japan (HVJ). HVJ-liposome has a very high fusion activity with a cellular membrane, as compared to general liposomes. When retrovirus is used as an expression vector, RetroNectin, fibronectin, polybrene and the like can be used as transfection reagents.

While the content of the above-mentioned expression vector in the pharmaceutical composition is not particularly limited and appropriately selected from a wide range, it is generally about 0.00001 to 100 wt % of the whole pharmaceutical composition.

By introducing the above-mentioned expression vector into a tissue (or cell) of an application target mammalian, the therapeutic or prophylactic agent of the present invention induces in vivo expression of the above-mentioned chimeric Hepatitis B virus core antigen polypeptide, induces production of an antibody to the epitope of VEGF and/or the epitope of angiopoietin-2 contained in the chimeric Hepatitis B virus core antigen polypeptide, and suppresses angiogenesis around the cancer tissues and inhibits the growth of cancer tissues by neutralization of the activity of the VEGF and/or angiopoietin-2 by the induced antibody. Various methods for introducing nucleic acids such as expression vector and the like into the body are known (T. Friedman, Science 244: 1275-1281 (1989)), and any introduction method can be adopted as long as it can induce in vivo expression of the above-mentioned chimeric Hepatitis B virus core antigen polypeptide, induce production of an antibody to the epitope of VEGF and/or the epitope of angiopoietin-2 contained in the chimeric Hepatitis B virus core antigen polypeptide, and treat or prevent cancer.

Examples of the method for introducing an expression vector into a mammalian tissue (or cell) in vivo include, but are not limited to, inner liposome method, electrostatic liposome method, HVJ-liposome method, HVJ-AVE liposome method, receptor-mediated transgene, particle gun method, naked DNA method, introduction method by positive electric charge polymer, electroporator method and the like.

Alternatively, cells such as blood cells, bone marrow cells and the like may be isolated from the application target mammal, the above-mentioned expression vector may be introduced into the cells ex vivo, after which the obtained cells containing the above-mentioned expression vector may be returned to the application target mammal.

Examples of the method for introducing an expression vector into a mammalian cell ex vivo include, but are not limited to, lipofection method, calcium phosphate coprecipitation method, DEAE-dextran method, direct DNA introduction method using glass microcapillary, electroporator method and the like.

The therapeutic or prophylactic agent of the present invention may be administered by any method as long as in the administration subject mammal, the agent induces in vivo expression of the above-mentioned chimeric hepatitis B virus core antigen polypeptide, induces production of an antibody to the specific epitope of VEGF and/or the specific epitope of angiopoietin-2 contained in the chimeric hepatitis B virus core antigen polypeptide, and treats or prevents cancer. Preferably, the therapeutic or prophylactic agent of the present invention parenterally administered in an amount sufficient to induce production of an antibody to the specific epitope of VEGF and/or the specific epitope of angiopoietin-2 contained in the chimeric hepatitis B virus core antigen polypeptide, and treats or prevents cancer. For example, injection via intravenous, intraperitoneal, subcutaneous, intradermal, intraadipose tissue, intramammary gland tissue, or intramuscular pathway; gas induced particle bombarding method (by electron gun and the like); a method in the form of collunarium and the like via a mucosal pathway, and the like are recited as examples of the administration methods. In one embodiment, the therapeutic or prophylactic agent of the present invention is injected subcutaneously or intramuscularly.

In one embodiment, the therapeutic or prophylactic agent of the present invention is subcutaneously administered by a needleless injector. The needleless injector is preferably a pressure injector. Examples of the needleless injector include, but are not limited to, ShimaJET (trade name, SHIMADZU CORPORATION), Twinject EZII (trade name, Japan chemical research), Syrijet (trade name, Keystone), ZENEO (trade name, Crossject) and the like. In this case, the therapeutic or therapeutic agent of the present invention can be provided as an injection preparation containing the above-mentioned expression vector and needleless injector, wherein the expression vector is enclosed in the needleless injector.

In one embodiment, the therapeutic or prophylactic agent of the present invention is administered subcutaneously, intradermally or intramuscularly with a gene gun. In this case, the above-mentioned expression vector may be applied onto the carrier particles such as colloidal gold particles and the like to be introduced into the body and used for administration. A technique for coating carrier particles with polynucleotide is known (see, for example, WO 93/17706). Finally, the expression vector can be prepared in an aqueous solution such as physiological saline and the like suitable for administration to the body.

To induce good immune responses, the therapeutic or improving agent of the present invention is preferably administered plural times at given intervals. While the frequency can be appropriately determined by monitoring the level of immune response, it is generally 2-10 times, preferably 2-6 times, more preferably 2, 3 or 4 times, most preferably 3 times.

The administration frequency is generally once per 1 week-1 year, preferably-once per 1-6 months.

In one embodiment, the therapeutic or prophylactic agent of the present invention is administered to a target mammal 3 times at 6 months intervals.

While the dose of the therapeutic or improving agent of the present invention depends on the immunogenicity of the epitope of VEGF and/or the epitope of angiopoietin-2 contained in the chimeric hepatitis B virus core antigen polypeptide encoded by the active ingredient expression vector in an administration subject mammal, those of ordinary skill in the art can determine the dose necessary for a good immune response by administering a given amount of an expression vector to an administration subject mammal, measuring the antibody titer specific to the epitope by a detection method such as ELISA and the like, and observing the immune response. Those of ordinary skill in the art appreciate that the immunogenicity of the therapeutic or prophylactic agent of the present invention also depends on the strength of the regulatory sequence such as promoter used for the expression vector as an active ingredient. Moreover, those of ordinary skill in the art can also control the dose of the therapeutic or prophylactic agent of the present invention with ease depending on the kind of the expression vector to be used.

When an expression vector encoding a chimeric hepatitis B virus core antigen polypeptide inserted with an amino acid sequence containing a specific epitope of VEGF and/or a specific epitope of angiopoietin-2 is administered, an immune response (preferably humoral immune response such as antibody production and the like) to the specific epitope of VEGF and/or the specific epitope of angiopoietin-2 in the expressed chimeric hepatitis B virus core antigen polypeptide is induced, and the activity of VEGF and/or angiopoietin-2 is neutralized with the antibody, whereby the angiogenesis around the cancer tissues can be suppressed and the growth of the cancer tissue can be inhibited. Accordingly, the subject of administration of the therapeutic or prophylactic agent of the present invention includes cancer patients, those having clinical history of cancer, non-cancer patients having a risk of developing cancer and the like. Cancer is treated by administering an expression vector encoding a chimeric hepatitis B virus core antigen polypeptide inserted with an amino acid sequence containing a specific epitope of VEGF and/or a specific epitope of angiopoietin-2 to cancer patients, thereby suppressing angiogenesis around the cancer tissues of the cancer patients and inhibiting growth of the cancer tissues. In addition, metastasis can be suppressed by suppressing angiogenesis around micrometastatic lesion in cancer patients. Recurrence of cancer can be suppressed by administering an expression vector encoding a chimeric hepatitis B virus core antigen polypeptide inserted with an amino acid sequence containing a specific epitope of VEGF and/or a specific epitope of angiopoietin-2 to those having clinical history of cancer, thereby suppressing angiogenesis around micrometastatic lesion possibly lying latent in the body of those having clinical history of cancer, and inhibiting growth of the cancer tissues. Moreover, the onset of cancer in non-cancer patients having a risk of developing cancer can be prevented by administering an expression vector encoding a chimeric hepatitis B virus core antigen polypeptide inserted with an amino acid sequence containing a specific epitope of VEGF and/or a specific epitope of angiopoietin-2 to the non-cancer patients.

All references cited herein, including patents and patent applications, are hereby incorporated in full by reference, to the extent that they have been disclosed herein.

The present invention is explained in more detail in the following by referring to Examples, which do not limit the present invention in any way.

EXAMPLES

Example 1

Preparation of Construct Expressing HBc-mVEGF (13aa) and HBc-hAng2 (16aa)

Plasmid pPLc3 (Accession number LMBP 2470) was purchased from BCCM/LMBP Plasmid Collection. DNA fragments encoding modified HBc, wherein a partial amino acid sequence (SEQ ID NO: 1) of mouse VEGF or a partial amino acid sequence (SEQ ID NO: 3) of human angiopoietin-2 is inserted between the amino acid residues 80 and 81 of HBc, were obtained by PCR and ligation. This DNA fragment was TA-cloned into pcDNA 3.1/V5-His TOPO TA Expression Kit (Invitrogen) to give the HBc-AngII ISS(−) vector. Similarly, PCR was performed using a template (plasmid pPLc3) and a primer set (HBcF and HBcR) to prepare a DNA fragment encoding a full-length polypeptide of HBc, and this DNA fragment was TA-cloned into the pcDNA 3.1/V5-His TOPO vector to give HBc-mVEGF expression vector and HBc-hAng2 expression vector. The amino acid sequences of the prepared HBc-mVEGF and HBc-hAng2 are shown in SEQ ID NOs: 28 and 30, respectively, and the nucleotide sequences encoding the amino acid sequences are shown in SEQ ID NOs: 27 and 29, respectively. The following regions correspond to the inserted sequences.

nucleotide Nos. 244-297 of SEQ ID NO: 27 (of these, nucleotide Nos. 250-288 encode SEQ ID NO: 1)
amino acid Nos. 81-98 of SEQ ID NO: 28 (of these, amino acid Nos. 83-95 correspond to SEQ ID NO: 1)
nucleotide Nos. 244-306 of SEQ ID NO: 29 (of these, nucleotide Nos. 250-297 encode SEQ ID NO: 3)
amino acid Nos. 81-101 of SEQ ID NO: 30 (of these, amino acid Nos. 83-98 correspond to SEQ ID NO: 3)

Example 2

Each expression vector (HBc, HBc-mVEGF, HBc-hAng2) prepared in Example 1 were introduced into BALB/c mice (female, 6-week-old) by electroporator. After immunization 3 times at 2 weeks intervals (0, 2, 4 w) and a lapse of 4 weeks, additional immunization was given (8 w). Colon26 (CT-26) cells in the growth stage Under culture in RPMI (10% FBS, pc/sm) were recovered by trypsin, and suspended in PBS to give a cell suspension having a concentration of $1 \times 10^7$ cells/mL in PBS. One week after the final additional immunization (9 w), the back of the immunized mouse was shaven, and the cell suspension (100 mL, $1 \times 10^6$ cells/mouse) was subcutaneously injected (Day 0). The tumor diameter was measured with a vernier caliper (tumor volume=long diameter×short diameter×short diameter÷2).

Figure 2:
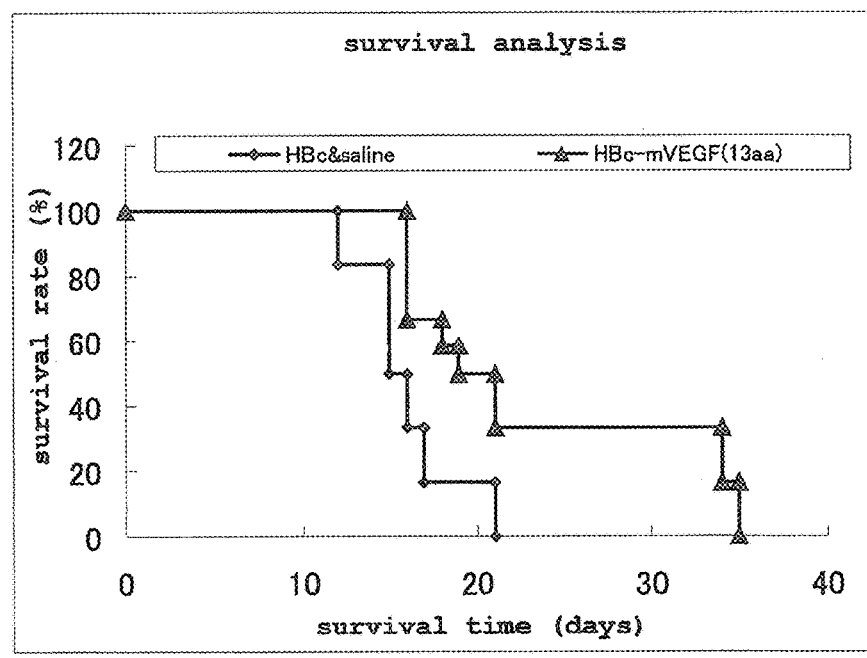

In the mice immunized with HBc-mVEGF and HBc-hAng2, the tumor growth was suppressed (FIG. 1), and the survival rate after tumor transplantation increased (FIG. 2) as compared to the negative control vector.

Example 3

Results

Production of DNA Vaccine for VEGF

Figure 3:
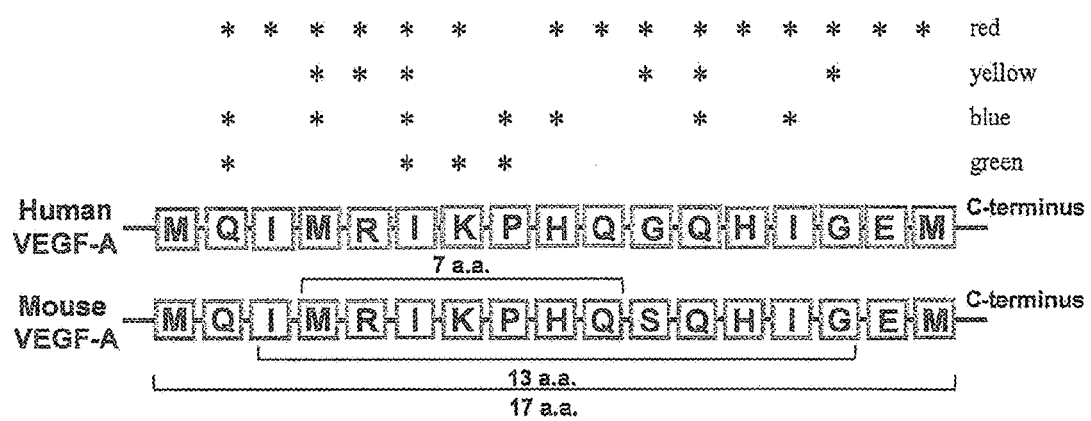
Figure 4:
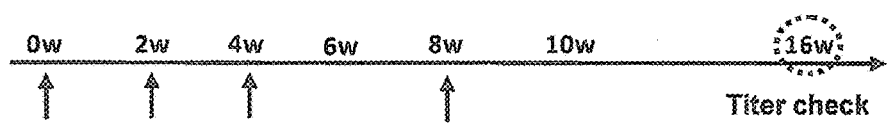
Figure 5:
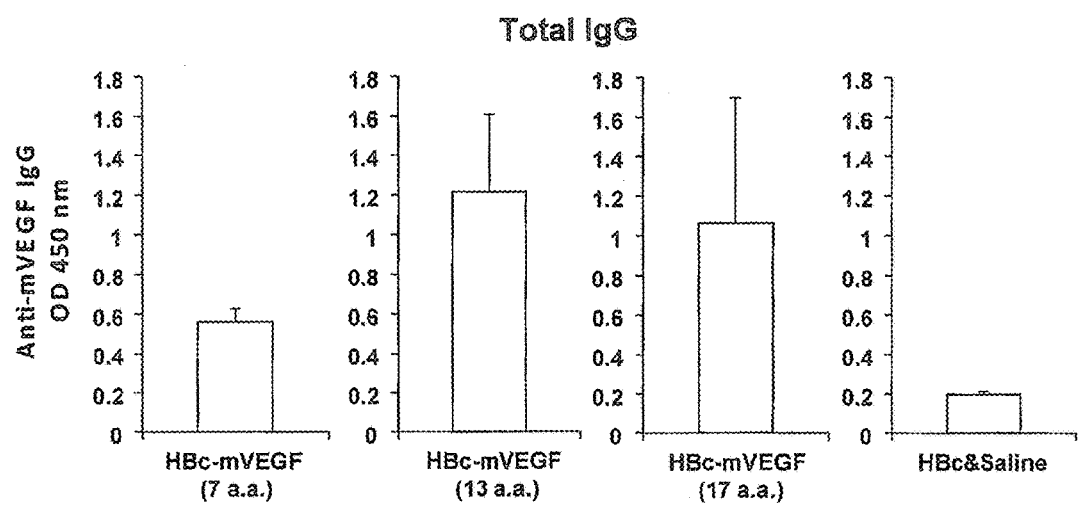
Figure 6:
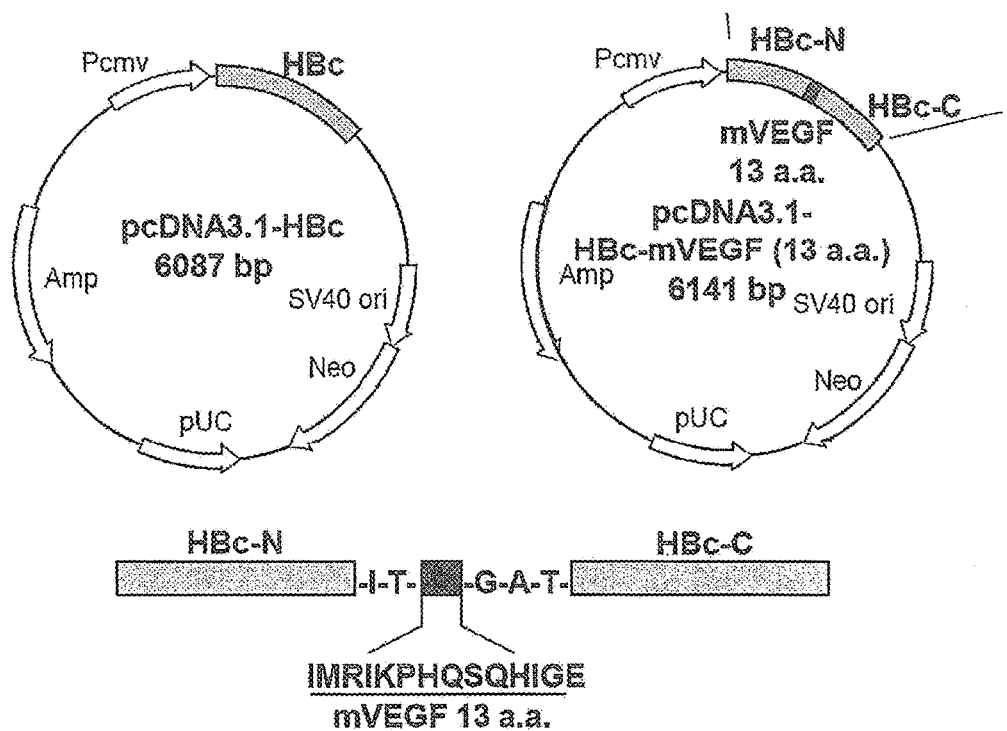

To confirm whether this DNA vaccine system would sufficiently induce anti-VEGF antibody production, BALB/c female mice were immunized with pcDNA3.1-HBc-mVEGF (7 a.a.) [HBc-mVEGF (7 a.a.)], pcDNA3.1-HBc [HBc] or saline, respectively, by intramuscular administration using electroporator, three times every two weeks and additional booster after third immunization (FIGS. 3 and 4). As a result, high titer of anti-VEGF antibody was not observed in HBc-mVEGF (7 a.a.) group compared to control (HBc and saline) group (FIG. 5). Because this 7 a.a. sequence might not be enough for B-cell epitope to induce anti-VEGF antibody, the long sequence was also designed as a candidate antigen, which covered the binding surface with bevacizumab, VEGFR-1 or VEGFR-2. 6 or 10 amino acids were added to core sequence, thereby creating the target 13-amino acid sequence (IMRIKPHQSQHIG; 13 a.a.) (SEQ ID NO: 1) and 17-amino acid sequence (MQIMRIKPHQSQHIGEM; 17 a.a.) (SEQ ID NO: 32), respectively (FIG. 3). Then, pcDNA3.1-mVEGF (13 a.a.) [HBc-mVEGF (13 a.a.)] and pcDNA3.1-mVEGF (17 a.a.) [HBc-mVEGF (17 a.a.)] were similarly constructed and vaccinated to mice. As shown in FIG. 5, both antigens successfully induced the production of anti-VEGF antibody. Relatively high titer of anti-VEGF was observed in the HBc-mVEGF (13 a.a.) group as compared to 17 a.a. and 7 a.a. groups (FIG. 5). Thus, 13 a.a. (IMRIKPHQSQHIG) (SEQ ID NO: 1) was decided as the antigen of VEGF DNA vaccine using HBc system (FIG. 6). The functionality of expression vector of HBc-mVEGF (13 a.a.) was confirmed in transfected COS-7 cells. Each construct expressed mRNA of the expected length and protein of expected molecular mass.

The titer of anti-VEGF antibody at eighth week, four weeks after third immunization were confirmed (FIG. 1*d*), and high titer was observed in HBc-mVEGF (13 a.a.) group (FIGS. 7*a* and 8). In the analysis of IgG subtypes, this immunization could lead to Th1-biased immune responses with predominant IgG2a and IgG2b production (FIG. 7*b*). The present inventors further confirmed whether the produced serum by immunization with HBc-mVEGF (13 a.a.) would recognize the recombinant mouse VEGF-A protein in western blot analysis. The specific binding of immunized serum with recombinant VEGF protein was confirmed using the commercial antibody against VEGF, VG-1 (FIG. 8).

Neutralizing Activity of Anti-VEGF Antibody Produced by VEGF DNA Vaccination

To examine the neutralizing activity of serum from vaccinated mice, we purified mouse IgG of serum using by Protein G column as described in method section. Treatment of immunized serum, but not control serum, significantly attenuated VEGF-A-induced ERK1/2 phosphorylation in HUVECs (FIG. 9). In the tube formation of HUVECs in matrigel, in the presence of EBM-2 with 0.4% FBS and 0.4% supplement, the addition of immunized serum also significantly attenuated the tube formation of HUVECs, as compared to the addition of control serum (FIG. 10).

(Method)

Measurement of Anti-mVEGF Antibody in Serum

Eight or sixteen weeks after first immunization, serum was collected from the immunized mice of all groups. Serum levels of anti-VEGF antibodies in these mice were measured by ELISA. Briefly, ELISA plates were coated with 5 μg/mL VEGF 13 a.a. peptide conjugated BSA in carbonate buffer overnight at 4° C. Serial dilutions (1:100 to 1:312500) of serum samples from the immunized mice were added to the wells, and HRP-conjugated mouse IgG (whole IgG; GE Health care, UK, each subtype; Abcam, UK) was added. After four washes with PEST, 3,3',5,5'-tetramethylbenzidine (TMB, Sigma-Aldrich, USA) was added. Production of the blue reaction product was stopped by adding 0.5 mol/L sulfuric acid, and the resulting end product (yellow) was read at 450 nm.

IgG Purification

Mouse serum was purified using by Protein G column according to the manufacturer's instructions (MAbTrap Kit; GE Healthcare, UK). Briefly, serum samples were adjusted to the composition of the binding buffer (20 mM sodium phosphate, pH 7.0). The Protein G column was washed out the ethanol preservative with distilled water and equilibrated with binding buffer. The diluted serum was applied and the column was wash with binding buffer until no material appears in the effluent. After that, IgG fraction was eluted by elution buffer (0.1 M glycine-HCl, pH 2.7) and concentrated by centrifugal filter (Amicon Ultra; Millipore, USA).

Tube Formation Assay

The tube formation assay using Matrigel (Becton-Dickinson, USA) was performed according to manufacturer's instructions. Briefly, matrigel was used to coat the wells of 24-well plates (0.25 mL per well) and was left to polymerize at 37° C. for 1 hour. After polymerization, HUVECs (100,000 cells) suspended in 0.3 ml of EBM-2 (containing 20% EGM-2 kit, 0.4% FBS and 20% supplement) with control serum or immunized serum, were added to each well. After 6 hours, the wells were photographed at 50-fold magnification in five randomized fields (Olympus) and the number of their tubular networks was counted by using ImageJ.

Western Blot Analysis

Briefly, for each of three independent experiments, total protein (10 μg) was isolated after indicated treatment using RIPA lysis buffer purchased from Millipore (Bedford, Mass.) with protease inhibitor cocktail (Roche, Mannhein, Germany), 10 mmol/L NaF, and 1 mmol/L $Na_3VO_4$; and size-fractioned by SDS-PAGE and transferred to Immobilon-P purchased from Millipore. The blotted protein was detected with antibodies against pERK and ERK (cell signaling technology); followed by the appropriate horseradish peroxidase (HRP)-conjugated secondary antibodies, and detected by ECL (Amersham, Arlington Heights, Ill.). Chemiluminescent signal was detected with a FujiFilm LAS-1000 camera and analyzed with Multi Gauge 3.2V software. Bands were quantified with ImageJ software.

INDUSTRIAL APPLICABILITY

The present invention provides a superior vaccine for the treatment or prophylaxis of cancer, which targets a tumor angiogenesis-related factor and shows a reduced risk of an adverse influence on the normal blood vessel function.

This application is based on patent application No. 2012-191717 filed in Japan (filing date: Aug. 31, 2012), the contents of which are incorporated in full herein.

The invention claimed is:

1. A therapeutic or prophylactic agent for cancer, comprising an expression vector encoding a chimeric Hepatitis B virus core antigen polypeptide inserted with an amino acid sequence comprising a specific epitope of VEGF,
   wherein the amino acid sequence comprising the specific epitope is inserted between the amino acid residues 80 and 81 of the hepatitis B virus core antigen polypeptide, and
   wherein the inserted amino acid sequence comprises the amino acid sequence shown in SEQ ID NO: 1 or 2.

2. The therapeutic or prophylactic agent according to claim 1, wherein the cancer is a solid tumor.

3. The therapeutic or prophylactic agent according to claim 2, wherein the solid tumor is any one kind selected from the group consisting of non-small cell lung cancer, colorectal cancer, breast cancer, pancreatic cancer, gastric cancer, uterine cancer and prostate cancer.

4. The therapeutic or prophylactic agent according to claim 1, wherein the inserted amino acid sequence comprises
   the amino acid sequence shown in SEQ ID NO: 32 or 33,
   a partial sequence of the amino acid sequence shown in SEQ ID NO: 32, which comprises the amino acid sequence shown in SEQ ID NO: 1, or
   a partial sequence of the amino acid sequence shown in SEQ ID NO: 33, which comprises the amino acid sequence shown in SEQ ID NO: 2.

5. The therapeutic or prophylactic agent according to claim 1, which is administered plural times.

6. The therapeutic or prophylactic agent according to claim 5, wherein the administration number is 2, 3 or 4.

7. The therapeutic or prophylactic agent according to claim 6, wherein the administration number is 3.

8. The therapeutic or prophylactic agent according to claim 1, which is administered 3 times at half year intervals.

9. An expression vector encoding a chimeric Hepatitis B virus core antigen polypeptide inserted with an amino acid sequence comprising a specific epitope of VEGF, which is for use in the treatment or prophylaxis of cancer,
   wherein the amino acid sequence comprising the specific epitope is inserted between the amino acid residues 80 and 81 of the hepatitis B virus core antigen polypeptide, and
   wherein the inserted amino acid sequence comprises the amino acid sequence shown in SEQ ID NO: 1 or 2.

10. The expression vector according to claim 9, wherein the cancer is non-small cell lung cancer, colorectal cancer, breast cancer, pancreatic cancer, gastric cancer, uterine cancer, or prostate cancer.

11. A method for the treatment or prophylaxis of cancer in a mammal, comprising administering an effective amount of an expression vector encoding a chimeric Hepatitis B virus core antigen polypeptide inserted with an amino acid sequence comprising a specific epitope of VEGF to the mammal,
- wherein the amino acid sequence comprising the specific epitope is inserted between the amino acid residues 80 and 81 of the hepatitis B virus core antigen polypeptide,
- wherein the inserted amino acid sequence comprises the amino acid sequence shown in SEQ ID NO: 1 or 2, and
- wherein the expression vector is administered to a mouse when the inserted amino acid sequence comprises the amino acid sequence shown in SEQ ID NO: 1, and the expression vector is administered to a human when the inserted amino acid sequence comprises the amino acid sequence shown in SEQ ID NO: 2.

12. The method according to claim 11, wherein the cancer is a solid tumor.

13. The method according to claim 12, wherein the solid tumor is any one kind selected from the group consisting of non-small cell lung cancer, colorectal cancer, breast cancer, pancreatic cancer, gastric cancer, uterine cancer and prostate cancer.

14. The method according to claim 11, wherein the inserted amino acid sequence comprises
- the amino acid sequence shown in SEQ ID NO: 32 or 33,
- a partial sequence of the amino acid sequence shown in SEQ ID NO: 32, which comprises the amino acid sequence shown in SEQ ID NO: 1, or
- a partial sequence of the amino acid sequence shown in SEQ ID NO: 33, which comprises the amino acid sequence shown in SEQ ID NO: 2.

15. The method according to claim 11, wherein the expression vector is administered plural times.

16. The method according to claim 15, wherein the expression vector is administered 2, 3 or 4 times.

17. The method according to claim 16, the expression vector is administered 3 times.

18. The method according to claim 11, wherein the expression vector is administered 3 times at half year intervals.

* * * * *